United States Patent
Fernandez-Valle

(10) Patent No.: US 9,408,832 B2
(45) Date of Patent: *Aug. 9, 2016

(54) LIM KINASEMODULATING AGENTS FOR NEUROFIBROMATOSES THERAPY AND METHODS FOR SCREENING FOR SAME

(71) Applicant: Cristina Fernandez-Valle, Oviedo, FL (US)

(72) Inventor: Cristina Fernandez-Valle, Oviedo, FL (US)

(73) Assignee: University of Central Florida Research Foundation, Inc., Orlando, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/385,211

(22) PCT Filed: Mar. 13, 2013

(86) PCT No.: PCT/US2013/030849
§ 371 (c)(1),
(2) Date: Sep. 15, 2014

(87) PCT Pub. No.: WO2013/138456
PCT Pub. Date: Sep. 19, 2013

(65) Prior Publication Data
US 2015/0105441 A1  Apr. 16, 2015

Related U.S. Application Data

(60) Provisional application No. 61/610,744, filed on Mar. 14, 2012, provisional application No. 61/641,624, filed on May 2, 2012, provisional application No. 61/738,654, filed on Dec. 18, 2012.

(51) Int. Cl.
| | |
|---|---|
| *A61K 48/00* | (2006.01) |
| *C07H 21/02* | (2006.01) |
| *C07H 21/04* | (2006.01) |
| *A61K 31/427* | (2006.01) |
| *A61K 31/185* | (2006.01) |
| *A61K 31/38* | (2006.01) |
| *A61K 31/4709* | (2006.01) |
| *A61K 31/498* | (2006.01) |
| *A61K 31/55* | (2006.01) |
| *C12N 15/113* | (2010.01) |
| *G01N 33/50* | (2006.01) |
| *A61K 31/422* | (2006.01) |

(52) U.S. Cl.
CPC ............. *A61K 31/427* (2013.01); *A61K 31/185* (2013.01); *A61K 31/38* (2013.01); *A61K 31/422* (2013.01); *A61K 31/4709* (2013.01); *A61K 31/498* (2013.01); *A61K 31/55* (2013.01); *C12N 15/113* (2013.01); *C12N 15/1137* (2013.01); *C12Y 207/11001* (2013.01); *G01N 33/502* (2013.01); *G01N 33/5011* (2013.01); *G01N 33/5014* (2013.01); *G01N 33/5058* (2013.01); *C12N 2310/11* (2013.01); *C12N 2310/12* (2013.01); *C12N 2310/14* (2013.01); *C12N 2310/141* (2013.01); *G01N 2333/912* (2013.01); *G01N 2500/04* (2013.01); *G01N 2500/10* (2013.01)

(58) Field of Classification Search
CPC .............................. A61K 48/00; C12N 15/111
See application file for complete search history.

(56) References Cited

U.S. PATENT DOCUMENTS

| | | |
|---|---|---|
| 5,010,175 A | 4/1991 | Rutter et al. |
| 5,283,317 A | 2/1994 | Saifer et al. |
| 5,288,514 A | 2/1994 | Ellman |
| 5,506,337 A | 4/1996 | Summerton et al. |
| 5,519,134 A | 5/1996 | Acevedo et al. |
| 5,525,735 A | 6/1996 | Gallop et al. |
| 5,539,083 A | 7/1996 | Cook et al. |
| 5,549,974 A | 8/1996 | Holmes |
| 5,569,588 A | 10/1996 | Ashby et al. |
| 5,593,853 A | 1/1997 | Chen et al. |
| 5,641,673 A | 6/1997 | Haseloff et al. |
| 5,705,151 A | 1/1998 | Dow et al. |
| 7,056,704 B2 | 6/2006 | Tuschl et al. |
| 7,078,196 B2 | 7/2006 | Tuschl et al. |
| 2004/0014047 A1 | 1/2004 | Cowsert et al. |
| 2004/0053411 A1 | 3/2004 | Cullen et al. |
| 2005/0075492 A1 | 4/2005 | Chen et al. |
| 2005/0277139 A1 | 12/2005 | Bentwich et al. |
| 2006/0110440 A1 | 5/2006 | Glover et al. |
| 2006/0130716 A1 | 6/2006 | Reyes-taboada et al. |
| 2006/0160764 A1 | 7/2006 | Friedman et al. |
| 2007/0009915 A1 | 1/2007 | Wang |
| 2007/0099193 A1 | 5/2007 | Wang |
| 2007/0099196 A1 | 5/2007 | Kauppinen et al. |
| 2011/0020816 A1 | 1/2011 | Chen et al. |
| 2011/0091510 A1 | 4/2011 | Lele et al. |
| 2011/0224286 A1 | 9/2011 | Yu et al. |
| 2011/0251255 A1 | 10/2011 | Chakrabarti |
| 2012/0034236 A1 | 2/2012 | Chakrabarti |

OTHER PUBLICATIONS

McConnell et al., "The Cytosensor Microphysiometer: Biological Applications of Silicon Technology", Science, 1992, vol. 257, pp. 1906-1912.

(Continued)

*Primary Examiner* — Amy Bowman
(74) *Attorney, Agent, or Firm* — Timothy H. Van Dyke; Beusse, Wolter, Sanks & Maire, PLLC

(57) ABSTRACT

Disclosed herein are methods of treating a patient at risk of developing or having a neurofibromatosis or a sporadic schwannoma. In exemplary embodiments, the method involves administering to a subject in need an effective amount of a LIMK modulating agent. Also disclosed are compounds newly identified to be inhibitors of Merlin-null Schwann cell proliferation and/or survival.

16 Claims, 10 Drawing Sheets

(56) References Cited

OTHER PUBLICATIONS

DeWitt et al, ""Diversomers": An approach to nonpeptide, nonoligomeric chemical diversity", Proc. Natl. Acad. Sci. U.S.A., 1993, vol. 90, pp. 6909-6913.
Erb et al., "Recursive deconvolution of combinatorial chemical libraries", Proc. NatL. Acad. Sci. U.S.A., 1994, vol. 91, pp. 11422-11426.
Zuckermann et al., "Discovery of Nanomolar Ligands for 7-Transmembrane G-Protein-Coupled Receptors from a Diverse N-(Substituted)glycine Peptoid Library", J. Med. Chem., 1994, vol. 37, pp. 2678-2685.
Carell et al., "A Novel Procedure for the Synthesis of Libraries Containing Small Organic-Molecules", Angew. Chem. Int. Ed. Engl., 1994, vol. 33, pp. 2059-2061.
Carell et al., "A Solution-Phase Screening Procedure for the Isolation of Active Compounds from a Library of Molecules", Angew. Chem. Int. Ed. Engl., 1994, vol. 33, pp. 2061-2064.
Gallop et al., "Applications of Combinatorial Technologies to Drug Discovery. 1. Background and Peptide Combinatorial Libraries", J. Med. Chem., 1994, vol. 37, pp. 1233-1251.
Lam, "Application of combinatorial library methods in cancer research and drug discover", Anticancer Drug Des., 1997, vol. 12, pp. 145-167.
Manetti, Fabrizio, "LIMK Kinases Are Attractive Targets with Many Macromolecular Partners and Only a Few Small Molecule", Published online in Wiley Online Library (wileyonlinelibrary.com) DOI 10.1002/med.20230, Jan. 16, 2011.
Ross-McDonald, P., et al., "Identification of a nonkinase target mediating cytotoxicity of novel kinase inhibitors", Mol Cancer Ther, 2008, vol. 7(11), pp. 3490-3498.
Scott, R., et al., "LIM kinases are required for invasive path generation by tumor and tumor-associated stromal cells", Journal of Cell Biology, 2010, vol. 191, pp. 170-185.
Ozawa, T.,et al., "The Neurofibromatosis Type 1 gene product neurofibromin enhances cell motility by regulating actin filament dynamics via the Rho-ROCK-LIMK2-cofilin pathway", J. Biol Chem, 2005, vol. 280, pp. 39524-39533.
Gunthand et al., "Comparative Performance of High-Density Oligonucleotide Sequencing and Dideoxynucleotide Sequencing of HIV Type 1 pol from Clinical Samples", AIDS Res. Hum. Retroviruses, 1998, vol. 14, pp. 869-876.
Kozal et al., "Extensive Polymorphisms observed in HIV-1 Clade B protease gene using high density oligonucleotide arrays", Nat. Med., 1996, vol. 2, pp. 753-759.
Matson et al., "Biopolymer Synthesis on Polypropylene supports: Oligonucleotide Arrays", Anal. Biochem., 1995, vol. 224, pp. 110-106.
Lockhart et al., "Expression Monitoring by Hybridization to High Density Oligonucleotide Arrays", Nat. Biotechnol., 1996, vol. 14, pp. 1675-1680.
Gingeras et al., "Simultaneous Genotyping and Species Identification Using Hybridization Pattern Recognition Analysis of Generic *Mycobacterium* DNA Arrays", Genome Res., 1998, vol. 8, pp. 435-448.
Menza, M et al, "Development of a high-throughput screening method for LIM kinase 1 using a luciferase-based assay of ATP consumption", Journal of Biomolecular Screening, 2011, vol. 17, No. 4, pp. 460-468.
Hacia et al., "Two color hybridization analysis using high density Oligonucleotide Arrays and energy transfer dyes", Nucleic Acids Res., 1998, vol. 26, pp. 3865-3866.
Merrifield, R.B., "Solid Phase Peptide Synthesis. I. The Synthesis of a Tetrapeptide", J. Am. Chem. Soc., 1963, vol. 85, pp. 2149-2154.
Geysen et al., "Strategies for epitope analysis using peptide synthesis", J. Immun. Meth., 1987, vol. 102, pp. 259-274.

Frank & Doring, "Simultaneous Multiple Peptide Synthesis Under Continuous Flow Conditions on Cellulose Paper Discs as Segmental Solid Supports", Tetrahedron, 1988, vol. 44, pp. 6031-6040.
Fodor et al., "Light-Directed, Spatially Addressable Parallel Chemical Synthesis", Science, 1991, vol. 251, pp. 767-777.
Sheldon et al., "Matrix DNA Hybridization", Clinical Chemistry, 1993, vol. 39, No. 4, pp. 718-719.
Furka, "General method for rapid synthesis of multicomponent peptide mixtures", Int. J. Pept. Prot. Res., 1991, vol. 37, pp. 487-493.
Houghton et al., "Generation and use of synthetic peptide combinatorial libraries for basic research and drug discovery", Nature, 1991, vol. 354, pp. 84-88.
Hobbs et al., ""Diversomers": An approach to nonpeptide, nonoligomeric chemical diversity", Proc. Nat. Acad. Sci. USA, 1993, vol. 90, pp. 6909-6913.
Hagihara et al., "Vinylogous Polypeptides: An Alternative Peptide Backbone", J. Amer. Chem. Soc., 1992, vol. 114, pp. 65-68.
Hirschmann et al., "Nonpeptidal Peptidomimetics with a 8-D-Glucose Scaffolding. A Partial Somatostatin Agonist Bearing a Close Structural Relationship to a Potent, Selective Substance P Antagonist", J. Amer. Chem. Soc., 1992, vol. 114, pp. 9217-9218.
Chen et al., "Analogous" Organic Synthesis of Small-Compound Libraries: Validation of Combinatorial Chemistry in Small-Molecule Synthesis, J. Amer. Chem. Soc., 1994, vol. 116 pp. 2661-2662.
Cho et al., "An Unnatural Biopolymer", Science, 1993, vol. 261, pp. 1303-1305.
Campbell et al., "Phosphonate Ester Synthesis Using a Modified Mitsunobu Condensation", J. Org. Chem., 1994, vol. 59, pp. 658-660.
Vaughn et al., "Human Anti-bodies with Sub-nanomolar affinities Isolated from a Large Non-immunized phage Display Library", Nature Biotechnology, 1996, vol. 14, No. 3, pp. 309-314.
Liang et al., "Parallel Synthesis and Screening of a Solid Phase Carbohydrate Library", Science, 1996, vol. 274, pp. 1520-1522.
Vatolin, et al , "A Novel Method to Detect Functional MicroRNA Targets", J Mol Biol, 2006, vol. 358, pp. 983-996.
Tsuda, et al, "Synthetic microRNA and double-stranded RNA targeting the 3'-untranslated region of HER/2neu mRNA inhibit HER/2 protein expression in ovarian cancer cells", Int J Oncol, 2005, vol. 27, pp. 1299-1306.
Haseloff et al. "Simple RNA enzymes with new and highly specific endoribonuclease activities", Nature, 1988, vol. 334, pp. 585-591.
Cech, "The chemistry of selfsplicing RNA and RNA enzymes", Science, 1987, vol. 236, pp. 1532-1539.
Cech, "Self-Splicing of Group I Introns", Ann. Rev. Biochem., 1990, vol. 59, pp. 543-568.
Cech, "Engineering and design: Ribozyme engineering", Curr. Opin. Struct. Biol., 1992, vol. 2, pp. 605-609.
Couture & Stinchcomb, "Anti-gene therapy: the use of ribozymes to inhibit gene function", Trends Genet., 1996, vol. 12, pp. 510-515.
Bonner et al, "Reduction in the rate of DNA Reassociation by Sequence Divergence", J. Mol. Biol. , 1973, vol. 81, pp. 123-135.
Song Y, et al., "Application of lentivirus-mediated RNAi in studying gene function in mammalian tooth development", Dev Dyn, 2006, vol. 235, pp. 1334-1344.
Tal, J., "Adeno-Associated Virus-Based Vectors in Gene Therapy", J. Biomed. Sci. , 2000, vol. 7, pp. 279-291.
Monahan and Samulski, "AAV vectors: is clinical success on the horizon?", Gene Therapy, 2000, vol. 7, pp. 24-30.
Kay et al., "Viral vectors for gene therapy: the art of turning infectious agents into vehicles of therapeutics", Nature Medicine, 2001, vol. 7, pp. 33-40.
Fraley, R., et al., "New generation liposomes: the engineering of an efficient vehicle for intracellular delivery of nucleic acids", Trends Biochem. Sci., 1981, vol. 6, pp. 77-80.
Findeis et al., "Targeted Delivery of DNA for Gene-Therapy Via Receptors", Trends in Biotechnol., 1993, vol. 11, pp. 202-205.
Wu & Wu, "Receptor-mediated Gene Delivery and Expression in Vivo", J. Biol. Chem., 1988, vol. 263, pp. 621-624.

(56) References Cited

OTHER PUBLICATIONS

Wu et al., "Incorporation of Adenovirus into a Ligand-based D N A Carrier System Results in Retention of Original Receptor Specificity and Enhances Targeted Gene Expression", J. Biol. Chem., 1994, vol. 269, pp. 11542-11546.

Zenke et al., "Receptor-mediated endocytosis of transferrin-polycation conjugates: An efficient way to introduce DNA into hematopoietic cells", Proc. Natl. Acad. Sci. U.S.A., 1990, vol. 87, pp. 3655-3659.

Wu et al., "Receptor-mediated Gene Delivery in Vivo", J. Biol. Chem., 1991, vol. 266, pp. 14338-14342.

Zervos et al., "Mxi1, a Protein that Specifically Interacts with Max to bind Myc-Max Recognition Sites", Cell, 1993, vol. 72, 223-232.

Madura et al., "N-recognin/Ubc2 Interactions in the N-end Rule Pathway", J. Biol. Chem., 1993, vol. 268, pp. 12046-12054.

Bartel et al., "Elimination of false positives that Arise in Using the Two-Hybrid System", BioTechniques, 1993, vol. 14, pp. 920-924.

Iwabuchi et al., "Use of the two-hybrid system to identify the domain of p53 involved in oligomerization", Oncogene, 1993, vol. 8, pp. 1693-1696.

Sjolander & Urbaniczky, "Integrated Fluid Handling System for Biomolecular Interaction Analysis", Anal Chem., 1991, vol. 63, pp. 2338-2345.

Szabo et al., "Surface plasmon resonance and its use in biomolecular interaction analysis (BIA)", Curr. Opin. Struct. Biol., 1995, vol. 5, pp. 699-705.

A                          B

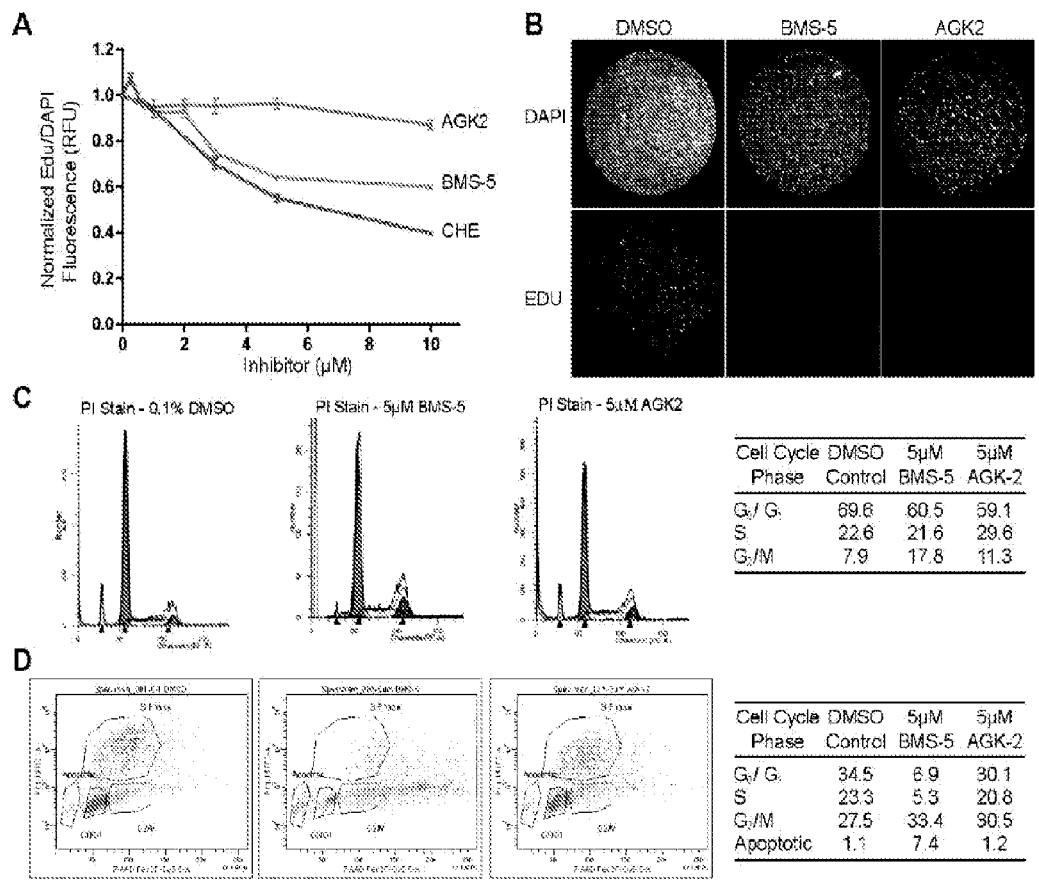
FIG. 11A-D

LIM KINASE MODULATING AGENTS FOR NEUROFIBROMATOSES THERAPY AND METHODS FOR SCREENING FOR SAME

STATEMENT REGARDING FEDERALLY SPONSORED RESEARCH OR DEVELOPMENT

This invention was made the Government support under agency contract/grant No. R01 DCO10189 awarded by the National Institutes of Health and under DAMD17-03-1-0211 awarded by the US Army Medical Research Acquisition Activity. The Government has certain rights in this invention.

BACKGROUND

Neurofibromatoses (NF) are genetic disorders of the nervous system. NF comprises three types of disease: Neurofibromatosis 1 (NF-1), Neurofibromatosis 2 (NF-2), and Schwannomatosis. They all have different genetic origins. However, they have a common feature: the development of tumors of the nervous system, particularly of the nerve sheath cell known as a Schwann cell. NF-1 is characterized by the development of neurofibromas associated with peripheral nerves. These benign tumors consist of various cell types, namely a mixture of Schwann cells, perennial fibroblasts and mast cells. The frequency of occurrence is 1 in 3000 persons. The second type, NF2, can be diagnosed by the presence of bilateral vestibular schwannomas, but schwannomas on other cranial and spinal nerves, and meningiomas and ependymomas occur as well. Schwannomas are also benign tumors, and consist of Schwann cells. The frequency of occurrence is approximately 1 in 25,000 persons. The third type of NF is Schwannomatosis, which presents with multiple schwannomas, but not involving the vestibular branch of the auditory nerve. A common and unique feature of this type of NF is severe unrelenting pain. The frequency of occurrence is about 1 in 40,000 persons. As a result, NF patients can suffer learning disabilities, hearing loss, imbalance, blindness, deformation, pain and higher mortality than the unaffected population. Currently, there are no known approved drug therapies for the treatment of NF.

In NF1 and NF2, there is a defect in tumor suppressor proteins, neurofibromin and merlin, respectively. One genetic mutation, INI1, also called SMARCB2 has been associated with Schwannomatosis. Consequently, abnormal Schwann cells present altered proliferation patterns, survival and cell morphology that lead to tumor formation. Normal Schwann cells undergo continuous morphological changes as they develop into myelinating and ensheathing cells. These changes are orchestrated by extracellular signals arising from the axon and basal lamina. The inventors have previously described a signaling pathway that involves the stimulation of ErbB2 and beta-integrin receptors by neuregulin and extracellular matrix molecules, respectively. Receptor stimulation leads to the activation of RhoGTPases, including Rac/Cdc42 and their effector kinase p21-activated kinase, PAK. A terminal kinase in this cascade is LIM kinase (LIMK). There are two LIMK family members, LIMK1 and LIMK2 (collectively "LIMK"). The major LIMK substrate is the actin depolymerizing and severing protein cofilin/ADF. LIMK-dependent phosphorylation of cofilin on serine 3 inactivates and promotes stabilization of the actin cytoskeleton. Moreover, LIMK translocates from focal adhesions, where it modulates cell morphology and motility, to the nucleus where it regulates cell cycle progression and cytokinesis. LIMK can also phosphorylate the cyclic-AMP responsive element-binding protein (CREB) in response to Cdc42/Rac-PAK1 activation suggesting transcriptional regulation activity as well. Recently, it was shown that LIMK signaling further promotes cell survival by p53-mediated transcriptional regulation.

BRIEF DESCRIPTION OF THE DRAWINGS

FIGS. 11A-D. Phenotypic Proliferation Assays. (A) Merlin-null Schwann cells (384-well format) were treated with the indicated compounds and concentrations for 24 hours and labeled with EdU during the last 9 hours. Incorporation of EdU into S-phase cells was read on a Biotek H1 Hybrid reader. (B) The plate was also imaged with a Trophos high resolution fluorescence Plate Runner. (C). Merlin-null Schwann cells were grown in 6-well format and were treated with 5 uM compounds for 22 hours, then labeled with PI. The cell population profile is shown and was analyzed using the ModFit program. (D). Merlin-null Schwann cells were grown as in C but were labeled with BrdU during the final 3 hours of treatment then stained with 7AAD. The distribution of BrdU- and 7AAD-labelled cells is shown and was analyzed with Diva program. The BD Cantos II flow cytometer was used above.

DETAILED DESCRIPTION

Figure 1:
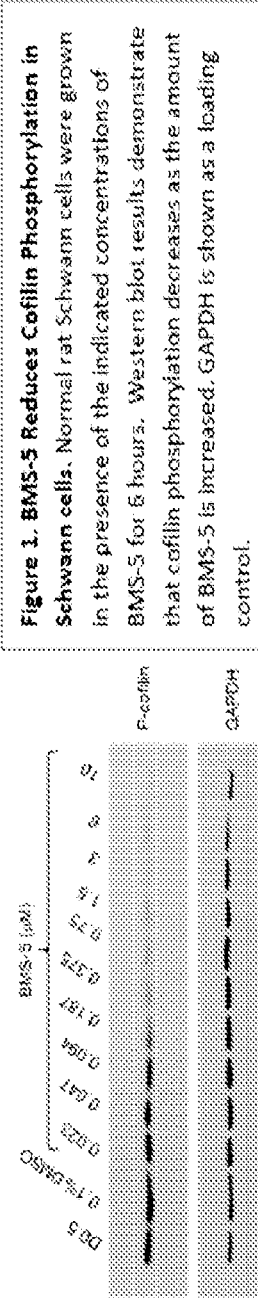
FIG. 1. BMS-5 Reduces Cofilin Phosphorylation in Schwann Cells. Normal rat Schwann cells were grown in the presence of the indicated concentrations of BMS-5 for 6 hours. Western blot results demonstrate that cofilin phosphorylation decreases as the amount of BMS-5 is increased.
Figure 1:
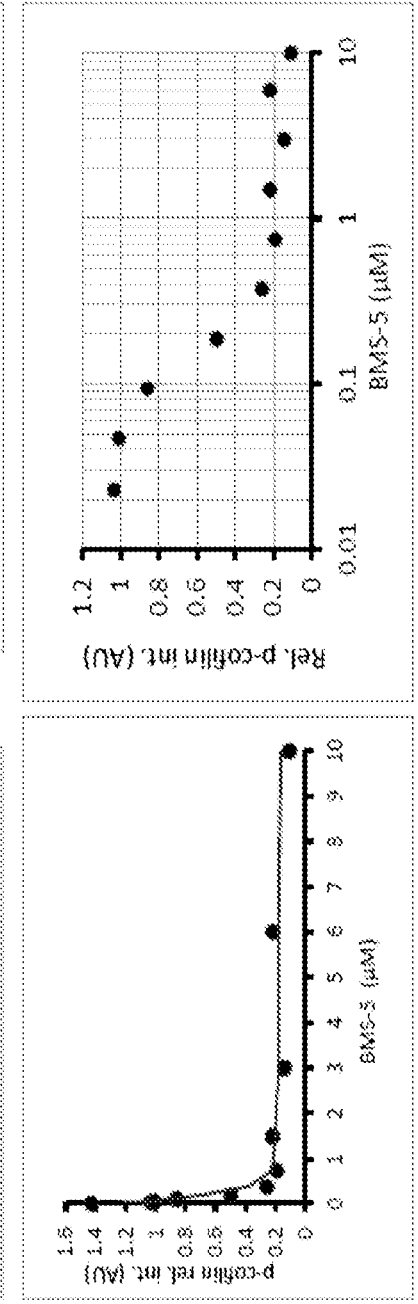

The present disclosure identifies a terminal kinase, LIMK, which is critical for Schwann cell cycle progression, cell survival, and regulation of cellular motility and myelination. The present inventors have found that the phosphorylation of LIMK and its substrate cofilin (which LIMK phosphorylates) increases within 5-10 days of loss of merlin function in mouse Schwann cells. Moreover, the present inventors have identified that particular LIMK modulating agents inhibit cofilin and CREB phosphorylation in mouse merlin null Schwann cells, via inhibition of LIMK. Further, the present inventors have found that specific LIMK modulating agents inhibited proliferation of merlin null Schwann Cells (MNSC) under various inhibitor concentrations. Thus, various methods and compositions are proposed herein for targeting intracellular targets for drug development to treat a neurofibromatosis or a sporadic schwannoma. In other embodiments, cost-effective methods for efficiently growing large numbers of mouse Merlin-null Schwann cells suitable for use in high-throughput screening campaigns of compound libraries have been developed. Further, the appropriate cellular conditions for conducting a successful high-throughput screening campaign have also been determined. Methods for screening compounds useful as modulators of LIMK are also described herein.

Definitions

Unless defined otherwise, all technical and scientific terms used herein have the same meaning as is commonly understood by one of ordinary skill in the art to which this disclosure belongs. All patents, applications, published applications and other publications are incorporated by reference in their entirety. In the event that there are a plurality of definitions for a term herein, those in this section prevail unless stated otherwise.

As used herein, the terms "administering" or "administration" of an agent, drug, or peptide to a subject includes any route of introducing or delivering to a subject a compound to perform its intended function. The administering or administration can be carried out by any suitable route, including orally, intranasally, parenterally (intravenously, intramuscularly, intraperitoneally, or subcutaneously), rectally, or topically. Administering or administration includes self-administration and the administration by another.

As used herein, the terms "disease," "disorder," or "complication" refers to any deviation from a normal state in a subject. In preferred embodiments, the methods and compositions are useful in the diagnosis and treatment of diseases where the expression or activity of a LIMK or cofilin, differs in subjects with disease, including development of NF and schwannomas in the absence of diagnosed NF, and subjects not having disease.

As used herein, by the term "effective amount" "amount effective," or the like, it is meant an amount effective at dosages and for periods of time necessary to achieve the desired result.

As used herein, the term "inhibiting" or "preventing" means causing the clinical symptoms of the disease state not to worsen or develop, e.g., inhibiting the onset of disease, in a subject that may be exposed to or predisposed to the disease state, but does not yet experience or display symptoms of the disease state.

As used herein, the term "expression" in the context of a gene or polynucleotide involves the transcription of the gene or polynucleotide into RNA. The term can also, but not necessarily, involves the subsequent translation of the RNA into polypeptide chains and their assembly into proteins.

As used herein, the terms "interfering molecule" refer to all molecules that have a direct or indirect influence on gene expression, such as the silencing of a target gene sequence. Examples of other interfering RNA molecules include siRNAs, short hairpin RNAs (shRNAs), single-stranded siRNAs, microRNAs (miRNAs), and dicer-substrate 27-mer duplexes. Examples of "RNA-like" molecules include, but are not limited to, siRNA, single-stranded siRNA, microRNA, and shRNA molecules that contain one or more chemically modified nucleotides, one or more non-nucleotides, one or more deoxyribonucleotides, and/or one or more non-phosphodiester linkages. Thus, siRNAs, single-stranded siRNAs, shRNAs, miRNAs, and dicer-substrate 27-mer duplexes are subsets of "interfering molecules." "Interfering molecules" also may include PMOs.

As used herein, the terms "neurofibromatoses," "neurofibromatosis," or "NF" refer to a genetic disorder of the nervous system. NF may comprise any one of Neurofibromatosis 1 (NF-1), Neurofibromatosis 2 (NF-2), and Schwannatosis, as well as spontaneously occurring schwannomas (sporadic schwannoma(s)) in the absence of a diagnosed NF condition, for example.

As used herein, the terms "phosphorothioate morpholino oligomer(s)," "a PMO" or "PMOs" refer to molecules having the same nucleic acid bases naturally found in RNA or DNA (i.e. adenine, cytosine, guanine, uracil or thymine), however, they are bound to morpholine rings instead of the ribose rings used by RNA. They may also be linked through phosphorodiamidate rather than phosphodiester or phosphorothioate groups. This linkage modification eliminates ionization in the usual physiological pH range, so PMOs in organisms or cells are uncharged molecules. The entire backbone of a PMO is made from these modified subunits.

As used herein, the term "antisense sequence" refers to an oligomeric compound that is at least partially complementary to a target nucleic acid molecule to which it hybridizes. In certain embodiments, an antisense compound modulates (increases or decreases) expression of a target nucleic acid. Antisense compounds include, but are not limited to, compounds that are oligonucleotides, oligonucleosides, oligonucleotide analogs, oligonucleotide mimetics, and chimeric combinations of these.

As used herein, the term "RNA interference" (RNAi) refers to a post-transcriptional gene silencing (PGSR) process whereby one or more exogenous small interfering RNA (siRNA) molecules are used to silence expression of a target gene.

As used herein, "siRNAs" (short interfering RNAs) refer to double-stranded RNA molecules, generally around 15-30 nucleotides in length, that are complementary to the sequence of the mRNA molecule transcribed from a target gene.

As used herein, "shRNAs" (small hairpin RNAs) are short "hairpin-turned" RNA sequences that may be used to inhibit or suppress gene expression.

As used herein, a "composition," "pharmaceutical composition" or "therapeutic agent" refers to a composition comprising a LIMK modulating agent and optionally a pharmaceutically acceptable carriers. In the case of an interfering molecule, for example, the interfering molecule may be combined with suitable a pharmaceutically acceptable carrier, such as phosphate-buffered saline.

As used herein, the term "subject" refers to any animal (e.g., a mammal), including, but not limited to, humans, which may be the recipient of a particular treatment.

As used herein, the terms "treating" or "treatment" or "alleviation" refers to both therapeutic treatment and prophylactic or preventative measures, wherein the objective is to prevent or slow down (lessen) the targeted pathologic condition or disorder.

As used herein, the term "LIMK" or "LIM kinases" refers to LIM kinase-1, LIM-kinase-2, or both and to additional family members not yet known. LIMK-1 and LIMK-2 belong to a small subfamily of kinases with a unique combination of 2 N-terminal LIM motifs, a PDZ domain connected to the proline/serine-rich regions, and a C-terminal protein kinase domain.[1] The LIM domains are cysteine/histidine-rich sequences coordinating zinc ions and constituted by two tandemly repeated zinc fingers separated by a two amino acid spacer.[1] LIM kinases have a highly basic short amino acid region (11 residues from Arg 495 to Arg 506 of LIMK1) in their activation loop, followed by a threonine (Thr508), which is similar to a regulatory phosphorylation site in several protein kinases.[1] Replacement of Thr508 with two glutamic acid residues (T508EE) yields a constitutively active LIMK1, while the D460N mutation results in a kinase-dead, catalytically inactive LIMK1.[1] LIMK2 contains a second basic amino acid-rich motif between the PDZ and the kinase domain, in addition to the basic amino acid-rich region found in the kinase domain of both LIMK1 and LIMK2.[1]

Cofilin is a protein with 70% sequence homology to ADF, making it part of the ADF/cofilin family of small ADP-binding proteins.[1] LIMK phosphorylates cofilin at Ser 3. Upon phosphorylation, cofilin is inactivated and is unable to sever F-actin into G-actin.[1] Cofilin activity may be restored by phosphatases, such as slingshot (SSH) and chronophin.[1] The Ser-3 phosphorylated form of cofilin also has regulatory function distinct from its action as an actin—severing and depolymerizing protein.

Through the novel recognition of the importance of LIMK activity in Schwann cell proliferation and function, the present application provides numerous methods and compositions useful for the treatment of a neurofibromatosis and spontaneously occurring schwannomas. In accordance with one aspect, there is provided a method for treating a neurofibromatosis in a subject. The method comprises administering to the subject an effective amount of a LIMK modulating agent, and derivatives or metabolites thereof. The neurofibromatosis may be NF1, NF2, Schwannomatosis, a sporadic schwannoma, and/or a disease otherwise characterized by the presence of a tumor of Schwann cell origin. The tumor of Schwann cell origin may be a schwannoma or a malignant peripheral nerve sheath tumor (MPNST). As set forth below, the inhibitor may include a ribozyme, an interfering molecule, a peptide, a small molecule, an antibody targeted to LIMK. LIMK modulating agent Derivatives According to certain embodiments, as used herein, derivatives of a compound (such as a LIMK modulating agent) include salts, esters, enol ethers, enol esters, acetals, ketals, orthoesters, hemiacetals, hemiketals, solvates, hydrates, metabolites or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, alk(en)(yn)yl, aryl, aralkyl, and cycloalkyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, alk(en)(yn)yl, aryl, aralkyl, or cycloalkyl. Pharmaceutically acceptable enol esters include, but are not limited to, derivatives of formula C=C(OC(O)R) where R is hydrogen, alkyl, alkenyl, alkynyl, aryl, aralkyl, or cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

According to further embodiments, derivatives may include, but are not limited to, specific substitutions of reactive constituents on or emanating from the LIMK modulating agent, and may include, but are not limited to, one or more of the following: a hydrogen, hydroxy, halo, haloalkyl, thiocarbonyl, alkoxy, alkenoxy, alkylaryloxy, aryloxy, arylalkyloxy, cyano, nitro, imino, alkylamino, aminoalkyl, thio, sulfhydryl, thioalkyl, alkylthio, sulfonyl, C1-C6 straight or branched chain alkyl, C2-C6 straight or branched chain alkenyl or alkynyl, aryl, aralkyl, heteroaryl, carbocycle, or heterocycle group or moiety, or CO2 R7 where R7 is hydrogen or C1-C9 straight or branched chain alkyl or C2-C9 straight or branched chain alkenyl group or moiety.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, alkyl refers to an unbranched or branched hydrocarbon chain. An alkyl group may be unsubstituted or substituted with one or more heteroatoms.

As used herein, alkenyl refers to an unbranched or branched hydrocarbon chain comprising one or more double bonds. The double bond of an alkenyl group may be unconjugated or conjugated to another unsaturated group. An alkenyl group may be unsubstituted or substituted with one or more heteroatoms.

As used herein, alkynyl refers to an unbranched or branched hydrocarbon chain comprising one of more triple bonds therein. The triple bond of an alkynyl group may be unconjugated or conjugated to another unsaturated group. An alkynyl group may be unsubstituted or substituted with one or more heteroatoms.

As used herein, alk(en)(yn)yl refers to an unbranched or branched hydrocarbon group comprising at least one double bond and at least one triple bond. The double bond or triple bond of an alk(en)(yn)yl group may be unconjugated or conjugated to another unsaturated group. An alk(en)(yn)yl group may be unsubstituted or substituted with one or more heteroatoms. Exemplary alkyl, alkenyl, alkynyl, and alk(en)(yn)yl groups herein include, but are not limited to, methyl, ethyl, propyl, isopropyl, isobutyl, n-butyl, sec-butyl, tert-butyl, isopentyl, neopentyl, tert-pentyl, isohexyl, allyl (propenyl) and propargyl (propynyl).

As used herein, "aryl" refers to aromatic monocyclic or multicyclic groups containing from 6 to 19 carbon atoms. Aryl groups include, but are not limited to groups such as unsubstituted or substituted fluorenyl, unsubstituted or substituted phenyl, and unsubstituted or substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl or isoquinolinyl.

As used herein, "halo," "halogen," or "halide" refers to F, Cl, Br or I.

As used herein, base refers to any compound that accepts protons in water or solvent. Thus, exemplary bases include, but are not limited to, alkali metal hydroxides and alkali metal alkoxides (i.e., MOR, wherein M is an alkali metal such as but not limited to potassium, lithium, or sodium and R is hydrogen, alkyl, alkenyl, alkynyl, or alk(en)(yn)yl) such as but not limited to potassium hydroxide, potassium tert-butoxide, potassium tert-pentoxide, sodium hydroxide, sodium tert-butoxide, lithium hydroxide, etc.); other hydroxides such as but not limited to magnesium hydroxide (Mg(OH)2), calcium hydroxide (Ca(OH)2), or barium hydroxide (Ba(OH)2); alkali metal hydrides (i.e., MH, wherein M is as defined above) such as but not limited to sodium hydride, potassium hydride, or lithium hydride; carbonates such as but not limited to potassium carbonate (K2CO3), sodium carbonate (Na2CO3), potassium bicarbonate (KHCO3), or sodium bicarbonate (NaHCO3); alkyl ammonium hydroxides, alkenyl ammonium hydroxides, alkynyl ammonium hydroxides, or alk(en)(yn)yl ammonium hydroxides such as but not limited to n-tetrabutyl ammonium hydroxide (TBAH); amines such as ammonia, diethylamine, 2,2,6,6-tetramethyl piperidine (HTMP), tertiary amines (such as but not limited to dimethylethyl amine, diisopropylethylamine, trimethylamine, triethylamine, tributylamine, N-methylmorpholine, N-methylpyrrolidine, 1,8-diazabicyclo[5.4.0]-7-undecene (DBU), 1,5-diazabicyclo[4.3.0]-5-nonene (DBN), or tetramethylenediamine (TMEDA)), aromatic amines (such as but not limited to pyridine, collidine, lutidine, picoline, quinoline, or N,N-dimethylaniline); alkali metal amides such as but not limited to lithium amide, lithium dimethylamide, lithium diisopropylamide (LDA), lithium tetramethylpiperidide (LiTMP), or alkali metal hexamethyldisilazanes (such as but not limited to potassium hexamethyldisilazane, (KHMDS), sodium hexamethyldisilazane (NaHMDS), or lithium hexamethyldisilazane (LiHMDS)); alkyl lithiums, alkenyl lithiums, alkynyl lithiums, or alk(en)(yn)yl lithiums such as but not limited to n-butyl lithium sec-butyllithium, isopropyllithium; alkyl magnesium halides, alkenyl magnesium halides, alkynyl magnesium halides, or alk(en)(yn)yl magnesium halides such as but not limited to methyl magnesium bromide.

As used herein, solvent refers to any liquid that completely or partially dissolves a solid, liquid, or gaseous solute, resulting in a solution such as but not limited to hexane, benzene, toluene, diethyl ether, chloroform, ethyl acetate, dichloromethane, carbon tetrachloride, 1,4-dioxane, tetrahydrofuran, glyme, diglyme, acetone, acetonitrile, dimethylformamide, dimethyl sulfoxide, dimethylacetamide, or N-methyl-2-pyrrolidone.

As used herein, dehydrating agent refers to any compound that promotes the formation of carboxamides from carboxylic acids, such as but not limited to thionyl chloride, sulfuryl chloride, a carbodiimide, an anhydride or a mixed anhydride, a phenol (such as but not limited to nitrophenol, pentafluorophenol, or phenol), or a compound of Formula (A):

wherein each of X and Y is independently an unsubstituted or substituted heteroaryl group (such as but not limited to imidazolyl, benzimidazolyl, or benzotriazolyl). Examples of dehydrating agents further include, but are not limited to, benzotriazole-1-yl-oxy-tris-(dimethylamino)-phosphonium hexafluorophosphate (BOP), N,N'-carbonyldiimidazole (CDI), 3-(diethoxyphosphoryloxy)-1,2,3-benzotriazin-4 (3H)-one (DEPBT), 1-ethyl-3-(3-dimethyllaminopropyl)carbodiimide (EDC), 2-(7-aza-1H-benzotriazole-1-yl)-1,1,3,3-tetramethyluronium hexafluorophosphate (HATU), 2-(1H-benzotriazole-1-yl)-1,1,3,3-tetramethyluronium hexafluorophosphate (HBTU), 1-hydroxybenzotriazole (HOBt), benzotriazole-1-yl-oxy-tris-pyrrolidino-phosphonium hexafluorophosphate (PyBOP), 2-(1H-benzotriazole-1-yl)-1,1,3,3-tetramethyluronium tetrafluoroborate (TBTU), O-(3,4-dihydro-4-oxo-1,2,3-benzotriazine-3-yl)-N,N,N,N-tetra methyluronium tetrafluoroborate (TDBTU), 3-(diethyloxyphosphoryloxy)-1,2,3-benzotriazin-4(3H)-one (DEPBT), dicyclohexylcarbodiimide (DCC), N,N'-diisopropylcarbodiimide (DIC), or 1-hydroxy-7-azabenzotriazole (HOAt). As used herein, acid refers to any compound that contains hydrogen and dissociates in water or solvent to produce positive hydrogen ions, as well as Lewis acids, including but not limited to hydrochloric acid, sulfuric acid, phosphoric acid, acetic acid, trihaloacetic acids (such as but not limited to trifluoroacetic acid or trichloroacetic acid), hydrogen bromide, maleic acid, sulfonic acids (such as but not limited to toluenesulfonic acids or camphorsulfonic acids), propionic acids (such as but not limited to (R)-chloropropionic acid), phthalamic acids (such as but not limited to N—[(R)-1-(1-naphthyl)ethyl]phthalamic acid), tartaric acids (such as but not limited to L-tartaric acid or dibenzyl-L-tartaric acid), lactic acids, camphoric acids, aspartic acids, or citronellic acids. It is to be understood that reactants, compounds, solvents, acids, bases, catalysts, agents, reactive groups, or the like may be added individually, simultaneously, separately, and in any order. Furthermore, it is to be understood that reactants, compounds, acids, bases, catalysts, agents, reactive groups, or the like may be pre-dissolved in solution and added as a solution (including, but not limited to, aqueous solutions). In addition, it is to be understood that reactants, compounds, solvents, acids, bases, catalysts, agents, reactive groups, or the like may be in any molar ratio.

It is to be understood that reactants, compounds, solvents, acids, bases, catalysts, agents, reactive groups, or the like may be formed in situ.

Enantiomers/Tautomers

LIMK modulating agents of the disclosure also include where appropriate all enantiomers and tautomers of the agents. The man skilled in the art will recognise compounds that possess an optical properties (one or more chiral carbon atoms) or tautomeric characteristics. The corresponding enantiomers and/or tautomers may be isolated/prepared by methods known in the art.

Stereo and Geometric Isomers

LIMK modulating agents of the disclosure may exist as stereoisomers and/or geometric isomers—e.g. they may possess one or more asymmetric and/or geometric centres and so may exist in two or more stereoisomeric and/or geometric forms. Contemplated herein is the use of all the individual stereoisomers and geometric isomers of those inhibitor agents, and mixtures thereof. The terms used in the claims encompass these forms, provided said forms retain the appropriate functional activity (though not necessarily to the same degree).

LIMK modulating agents of the disclosure also include all suitable isotopic variations of the agent or pharmaceutically acceptable salts thereof. An isotopic variation of LIMK modulating agent or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as 2H, 3H, 13C, 14C, 15N, 17O, 18O, 31P, 32P, 35S, 18F and 36C1, respectively. Certain isotopic variations of the agent and pharmaceutically acceptable salts thereof, for example, those in which a radioactive isotope such as 3H or 14C is incorporated, are useful in drug and/or substrate tissue distribution studies. Tritiated, i.e., 3H, and carbon-14, i.e., 14C, isotopes are particularly preferred for their ease of preparation and detectability. Further, substitution with isotopes such as deuterium, i.e., 2H, may afford certain therapeutic advantages resulting from greater metabolic stability, for example, increased in vivo half-life or reduced dosage requirements and hence may be preferred in some circumstances. Isotopic variations of the LIMK modulating agents and pharmaceutically acceptable salts thereof of this disclosure can generally be prepared by conventional procedures using appropriate isotopic variations of suitable reagents.

Solvates

The LIMK modulating agent agents also includes solvate forms of the agents. The terms used in the claims encompass these forms.

Polymorphs

The LIMK modulating agents also include their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

Embodiments of the disclosure further include LIMK modulating agents in prodrug form. Such prodrugs are generally compounds wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Metabolites

Also falling within the scope of this invention are the in vivo metabolic products of compounds of Table 3 described herein. A "metabolite" is a pharmacologically active product produced through metabolism in the body of a specified compound or salt thereof. Such products can result, for example, from the oxidation, reduction, hydrolysis, amidation, deamidation, esterification, deesterification, enzymatic cleavage, and the like, of the administered compound. Accordingly, the invention includes metabolites of compounds set forth in Table 3, including compounds produced by a process comprising contacting a compound of this invention with a mammal for a period of time sufficient to yield a metabolic product thereof.

Metabolites are identified, for example, by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolites, so long as they are not otherwise found in vivo, are useful in diagnostic assays for therapeutic dosing of the compounds of the invention.

In accordance with another aspect, there is provided a method of inhibiting proliferation of tumors comprised in whole or in part of Schwann cells and their derivatives in a subject. The method comprises administering an effective amount of an LIMK modulating agent as described herein to the subject to inhibit the expression or action of LIMK.

In accordance with other aspects, there are provided methods for screening compound libraries to identify selective compounds that will inhibit the activity of LIMK target, in cell models of neurofibromatosis, for example, and determine whether such compounds slow growth of tumor cells or cause them to die. In one specific embodiment, there is provided a method of screening for compounds capable of inhibiting LIMK. The method comprises determining the activity of a LIMK polypeptide without contact with a test compound. Thereafter, the method comprises determining the activity of said LIMK polypeptide upon contact of the test compound. The test compound that modulates activity of the LIMK polypeptide is identified as potential LIMK modulating agent. In one embodiment, the step of contacting is in or at the surface of a Schwann cell. The cell may be in vitro in some embodiments, else may be in a cell-free system.

According to another embodiment, disclosed herein are methods for screening of compound libraries to identify selective compounds that modulate activity of a LIMK target.

In accordance with another aspect, there is provided a method of screening for compounds capable of inhibiting LIMK. The method comprises contacting at least one LIMK modulating agent test compound with a LIMK polypeptide. In addition, the method comprises detecting binding of said at least one LIMK modulating agent test compound to said LIMK polypeptide, wherein a test compound which binds to the LIMK polypeptide is identified as a potential LIMK modulating agent.

In accordance with another aspect, there is provided a method of screening for compounds capable of inhibiting LIMK. The method comprises contacting a test compound with a LIMK polynucleotide. Further, the method includes detecting binding of the test compound to the LIMK polynucleotide, wherein a test compound that binds to a LIMK polynucleotide is identified as potential LIMK modulating agent.

In accordance with yet another aspect, there is provided a method for the preparation of a pharmaceutical composition useful for the prevention and/or treatment of a neurofibromatosis, a sporadic schwannoma, or a symptom thereof. The method comprises identifying a LIMK modulating agent in accordance with any method described herein. The method further includes combining of the LIMK modulating agent with an acceptable pharmaceutical carrier.

In accordance with yet another aspect, there is provided a pharmaceutical composition for the prevention and/or treatment of a neurofibromatosis, a sporadic schwannoma, or a symptom thereof, comprising a therapeutic agent which binds to a LIMK polypeptide.

In accordance with yet another aspect, there is provided a pharmaceutical composition for the prevention and/or treatment of a neurofibromatosis or sporadic schwannoma comprising a therapeutic agent which regulates the activity of a LIMK polypeptide. The therapeutic agent may be selected from the group consisting of a ribozyme, an interfering molecule, a peptide, a small molecule, an antibody targeted to LIMK, and combinations thereof.

In accordance with another aspect, there is provided a method for treating a condition in a subject in need. The method comprises administering to the subject an effective amount of a LIMK modulating agent, wherein the condition comprises a symptom of a neurofibromatosis or a sporadic schwannoma. The symptom may be one or more symptoms for NF1, NF2, Schwannomatosis and sporadic schwannomas, as described below.

According to another embodiment, what is provided is a method of screening for compounds capable of affecting neurofibromatosis. The method includes contacting at least one LIMK modulator test compound with at least one Merlin-null ($nf2^{ex2-/-}$) Schwann Cell; and monitoring growth or cytotoxicity of the at least one Merlin-null ($nf2^{ex2-/-}$) Schwann Cell. A test compound that modulates growth of or cytotoxicity to the at least one Merlin-null ($nf2^{ex2-/-}$) Schwann Cell is identified as a potential LIMK modulating agent. In a specific embodiment, the method is set up in a high throughput format, wherein the at least one Merlin-null ($nf2^{ex2-/-}$) Schwann Cell comprises a multiplicity of cell samples separated and disposed in individual wells in a multi-well plate. Moreover, a plurality of LIMK modulating agent test compounds may be individually tested on at least one cell sample of said multiplicity of cell samples.

In yet another embodiment, there is provided a high throughput screening system including a plurality of wells having a high transmittance portion through which cells present in the wells are optically observable in an area of observation; an optical detector configured to detect light emanating from the wells through the high transmittance portion; and a data processing unit configured to store data indicative of light intensity detected by the optical detector and corresponding to modulation of at least some of the cells, wherein the cells are Merlin-null ($nf2^{ex2-/-}$) Schwann Cells. In a typical example, the plurality of wells are located in a multiwell plate. The wells may have, but do not require, a transmittance portion made from a material selected from the group consisting of glass, quartz, cycloolefin, Aclar, polypropylene, polyethylene and polystyrene. Typically the multi-well plate includes up to 96 wells. Alternatively, the multiwell plate includes 96 wells or more. Furthermore, the plate may include 384 wells or greater. Typically, modulating activity is detected by ELISA, light emission, colorimetric measurements or enzymatic activity.

The compounds and methods described herein may be utilized in the treatment or prevention of symptoms of NF1, NF2, Schwannomatosis and/or sporadic schwannomas. In NF1, the most common symptom of NF1 is the appearance of multiple, painless, coffee-colored patches on the skin, known as café au lait spots. Other common symptoms are freckles in unusual places, such as the armpits, groin and under the breast, and bumps on or under the skin referred to as neurofibromas. Other symptoms of NF1 may include, but are not limited to, learning and behavior problems, such as an intelligence quotient of less than 90; attention deficit hyperactivity disorder (ADHD); and development of a tumor, which is usually non-cancerous, inside the optic nerve, referred to as an optic pathway glioma (OPG). Problems associated with an OPG include blurry vision, alteration of color perception, reduced field of vision, and squinting. Another common symptom of NF1 is the appearance of tiny brown spots in the iris (the colored, central part of the eye), also known as Lisch nodules. Additional symptoms include high blood pressure, an abnormally curved spine, e.g., scoliosis, reduced height and weight, leg bowing, migraines, and small, benign brain tumors.

One serious symptom that can affect a person with NF1 is a malignant peripheral nerve sheath tumor (MPNST). MPNST, typically forms from unexpected growth of a preexisting neurofibroma, particularly a plexiform neurofibroma. The first symptom is typically unexplained or sudden pain, in the area in or around existing tumors. Other symptoms may include swelling in the extremities (arms or legs); the swelling often is painless; difficulty in moving the extremity that has the tumor, including a limp; and soreness localized to the area of the tumor or in the extremity.

For NF2, the most common initial symptoms affect the ears, specifically the vestibulocochlear nerve that run from the ears to the brain. These symptoms include gradual and increasing hearing loss; a constant ringing or buzzing sound in the ears (tinnitus); balance problems, such as feeling dizzy, vertigo, nausea, and vomiting. Other common symptoms of a vestibular schwannomas are facial numbness, tongue weakness, facial pain, and benign (non-cancerous) brain tumors called meningiomas, which may cause headaches, vomiting, seizures, visual disturbances, personality changes, difficulty in speech, vision loss, fits or blackouts, memory and speech problems, a sensation of strange smells, loss of co-ordination, difficulty walking and speaking, flickering of the eyes, vomiting, stiff neck, unsteadiness and difficulty walking, facial weakness, double vision and difficulty speaking and swallowing.

Other symptoms include the development of one or more benign tumors, known as ependymomas, inside their spinal cord or brain ventricles which may cause back pain, muscle weakness, unpleasant physical sensations in certain parts of the body, such as numbness or tingling, buzzing or a "crawling" sensation on the skin. Just over half of people with NF2 develop benign tumors on or underneath the surface of their skin, referred to as schwannomas. They show as small, colored, raised patches of skin that are usually less than 2 cm across. Subcutaneous schwannomas are tumors in the form of lumps that develop underneath the skin. Many people with NF2 develop multiple subcutaneous schwannomas, which can grow to around the size of a golf ball. About a third of people with NF2 develop coffee-colored patches on their skin as mentioned above with NF1, called café au lait spots. Other symptoms include the development of peripheral neuropathy, which may lead to a feeling of "pins and needles" in the affected body part; numbness and a reduced ability to feel pain or temperature changes, particularly in the feet; a burning pain, usually in the feet and legs followed by the hands and arms as the neuropathy progresses; and muscle weakness. About two-thirds of people with NF2 develop cataracts. These are cloudy patches in the transparent structure at the front of the eye, known as the lens, which leave a person's vision blurred or misty.

For schwannomatosis, symptoms include development of multiple schwannomas everywhere in the body except on the vestibular nerve. The dominant symptom is pain, which develops as a schwannoma enlarges, compresses nerves, or presses on adjacent tissue. Some subjects experience additional neurological symptoms, such as numbness, tingling, or weakness in the fingers and toes. Individuals with schwannomatosis do not have neurofibromas. About one-third of individuals with schwannomatosis have tumors limited to a single part of the body, such as an arm, leg, or a segment of the spine. Some people develop many schwannomas such as along spinal nerves, while others develop only a few.

For sporadic schwannomas, individuals without NF1, NF2 or schwannomatosis can develop single or multiple schwannomas affected one or more spinal, cranial or peripheral nerves. Symptoms affect loss of function or decreased function of the affected area of the tumor and/or pain associated with the tumor site.

According to certain embodiments, provided are methods of preventing or treating a neurofibromatosis and a sporadic schwannoma in a subject or preventing or treating a subject exhibiting a symptom thereof comprising inhibiting LIMK targets. LIMK targets can be inhibited by a number of methods including silencing via an interfering molecule, e.g., siRNA, directed to a portion of the sequence described at the genbank accession numbers for LIMK. The structure for LIMK1, LIMK2, and isoforms thereof, are well-known in the art. An exemplary LIMK1 sequence is disclosed at accession no. NP_001191355.1 (SEQ ID NO: 1). See also ncbi.nlm.nih.gov/protein?term=limk1 and ncbi.nlm.nih.gov/protein?term=lim %20kinase %201 for additional LIMK1 sequences. An exemplary LIMK2 sequence is disclosed at accession no. BAA08312.1 (SEQ ID NO: 2). See also ncbi.nlm.nih.gov/protein?term=limk %202 and.ncbi.nlm.nih.gov/protein?term=lim %20kinase %202 for additional LIMK2 sequences. Corresponding nucleotide sequences for expressing any of these sequences, such as LIMK1 and LIMK2, are readily ascertainable by one skilled in the art using known techniques. As set forth below, the present invention incorporates agents that may inhibit the activity or expression of LIMK1 and/or LIMK2 polypeptides by targeting the same or by targeting nucleotide sequences for the expression thereof.

The following discussion will further describe the screening methods, compositions, and methods for treating and/or preventing neurofibromatosis or a symptom of a neurofibromatosis or sporadic schwannomas as described herein.

1. Screening Methods

The present invention provides for screening test compounds which bind to or modulate the activity of a LIMK polypeptide, or bind to and inhibit or affect expression of a LIMK polynucleotide. A test compound preferably binds to a LIMK polypeptide. More preferably, a test compound reduces LIMK activity, by at least about 10, preferably about 50, more preferably about 75, 90, or 100% relative to the absence of the test compound. One method of measuring the efficacy of a LIMK modulating agent, is the reduction in the number of NF2-inactivated Schwannoma cells.

1.1. Test Compounds

Test compounds relate to agents that potentially have therapeutic activity, i.e., bind to or modulate the activity of a LIMK polypeptide or bind to or affect expression of a LIMK polynucleotide. Test compounds can be pharmacologic agents already known in the art or can be compounds previously unknown to have any pharmacological activity. The compounds can be naturally occurring or designed in the laboratory. They may be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, Anticancer Drug Des. 12, 145, 1997.

Methods for the synthesis of molecular libraries are well known in the art (see, for example, DeWitt et al, Proc. Natl. Acad. Sci. U.S.A. 90, 6909, 1993; Erb et al. Proc. NatL. Acad. Sci. U.S.A. 91, 11422, 1994; Zuckermann et al., J. Med. Chem. 37, 2678, 1994; Cho et al., Science 261, 1303, 1993; Carell et al., Angew. Chem. Int. Ed. Engl. 33, 2059, 1994; Carell et al., Angew. Chem. Int. Ed. Engl. 33, 2061; Gallop et al., J. Med. Chem. 37, 1233, 1994).

1.2. High Throughput Screening

Test compounds can be screened for the ability to bind to and inhibit LIMK polypeptides or polynucleotides or LIMK activity or LIMK gene expression using high throughput screening. Using high throughput screening, many discrete compounds can be tested in parallel so that large numbers of test compounds can be quickly screened. The most widely established techniques utilize 96, 384 and 1536-well microtiter plates. The wells of the microtiter plates typically require assay volumes that range from 5 to 500 µl. In addition to the plates, many instruments, materials, pipettors, robotics, plate washers, and plate readers are commercially available to fit these multi-well formats. Alternatively, "free format assays," or assays that have no physical barrier between samples, can be used.

1.3. Binding Assays

For binding assays, the test compound is preferably, but not necessarily, a small molecule which binds to and occupies, for example, the active site of the LIMK polypeptide, such that normal biological activity is prevented. Examples of such small molecules include, but are not limited to, small peptides or peptide-like molecules as are described below.

In binding assays, either the test compound or the LIMK polypeptide can comprise a detectable label, such as a fluorescent, radioisotopic, chemiluminescent, or enzymatic label, such as horseradish peroxidase, alkaline phosphatase, or luciferase. Detection of a test compound which is bound to the LIMK polypeptide can then be accomplished, for example, by direct counting of radioemission, by scintillation counting, or by determining conversion of an appropriate substrate to a detectable product.

Those skilled in the art equipped with teachings herein will appreciate that there are multiple conventional methods of detecting binding of a test compound. For example, binding of a test compound to a LIMK polypeptide can be determined without labeling either of the interactants. A microphysiometer can be used to detect binding of a test compound with a LIMK polypeptide. A microphysiometer (e.g., CYTOSENSOR™) is an analytical instrument that measures the rate at which a cell acidifies its environment using a light-addressable potentiometric sensor (LAPS). Changes in this acidification rate can be used as an indicator of the interaction between a test compound and a LIMK polypeptide (McConnell et al., Science 257, 19061912, 1992).

In another alternative example, determining the ability of a test compound to bind to a LIMK polypeptide can be accomplished using a technology such as real-time Bimolecular Interaction Analysis (BIA) (Sjolander & Urbaniczky, Anal Chem. 63, 23382345, 1991, and Szabo et al., Curr. Opin. Struct. Biol. 5, 699705, 1995). BIA is a technology for studying biospecific interactions in real time, without labeling any of the interactants (e.g., BIAcore™) Changes in the optical phenomenon surface plasmon resonance (SPR) can be used as an indication of real-time reactions between biological molecules.

In yet another aspect of the invention, a LIMK polypeptide can be used as a "bait protein" in a two-hybrid assay or three-hybrid assay (see, e.g., U.S. Pat. No. 5,283,317; Zervos et al., Cell 72, 223232, 1993; Madura et al., J. Biol. Chem. 268, 1204612054, 1993; Bartel et al., BioTechniques 14, 920924, 1993; Iwabuchi et al., Oncogene 8, 16931696, 1993; and Brent WO94/10300), to identify other proteins which bind to or interact with the LIMK polypeptide and modulate its activity.

In many screening embodiments, it may be desirable to immobilize either the LIMK polypeptide (or polynucleotide) or the test compound to facilitate separation of bound from unbound forms of one or both of the interactants, as well as to accommodate automation of the assay. Thus, either the LIMK polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, glass, or magnetic beads). Any method known in the art can be used to attach the LIMK polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to a LIMK polypeptide (or polynucleotide) can be accomplished in any vessel suitable for containing the reactants. Examples of such vessels include microtiter plates, test tubes, and microcentrifuge tubes.

In specific embodiments, the LIMK polypeptide may be a fusion protein comprising a domain that allows the LIMK polypeptide to be bound to a solid support. For example, glutathione S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed LIMK polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either a LIMK polypeptide (or polynucleotide) or a test compound can be immobilized utilizing conjugation of biotin and streptavidin. Biotinylated LIMK polypeptides (or polynucleotides) or test compounds can be prepared from biotinNHS(Nhydroxysuccinimide) using techniques well known in the art (e.g., biotinylation kit, Pierce Chemicals, Rockford, 111.) and immobilized in the wells of streptavidin-coated 96 well plates (Pierce Chemical). Alternatively, antibodies which specifically bind to a LIMK polypeptide, polynucleotide, or a test compound, but which do not interfere with a desired binding site, such as the active site of the LIMK polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the LIMK polypeptide or test compound, enzyme-linked assays which rely on detecting an activity of the LIMK polypeptide, and SDS gel electrophoresis under non-reducing conditions.

Screening for test compounds which bind to a LIMK polypeptide or polynucleotide also can be carried out in an intact cell. Any cell which comprises a LIMK polypeptide or polynucleotide can be used in a cell-based assay system. A LIMK polynucleotide can be naturally occurring in the cell or can be introduced using techniques such as those described above. Binding of the test compound to a LIMK polypeptide or polynucleotide is determined as described above. In one embodiment, the cell is a Schwann cell, and in a particular embodiment it is a Schwannoma cell. In a particular embodiment, the cell is a NF2-inactivated Schwannoma cell.

1.4. Enzyme Assays

Test compounds can be tested for the ability to increase or decrease the LIMK activity of a LIMK polypeptide. Enzyme assays can be carried out after contacting either a purified LIMK polypeptide, a cell membrane preparation, or an intact cell with a test compound. A test compound which decreases the activity of a LIMK polypeptide by at least about 10, preferably about 50, more preferably about 75, 90, or 100% is identified as a potential therapeutic agent for use herein.

1.5. Gene Expression

In another embodiment, test compounds which increase or decrease LIMK gene expression are identified. A LIMK polynucleotide is contacted with a test compound, and the expression of an RNA or polypeptide product of LIMK polynucleotide is determined. The level of expression of appropriate mRNA or polypeptide in the presence of the test compound is compared to the level of expression of mRNA or polypeptide in the absence of the test compound. The test compound can then be identified as a modulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of LIMK mRNA or polypeptide expression in the cells can be determined by methods well known in the art for detecting mRNA or polypeptide. Either qualitative or quantitative methods can be used. The presence of polypeptide products of a LIMK polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into a LIMK polypeptide.

Such screening can be carried out either in a cell-free assay system or in an intact cell. Any cell which expresses a LIMK polynucleotide can be used in a cell-based assay system. The LIMK polynucleotide can be naturally occurring in the cell or can be introduced using techniques such as those described above. Either a primary culture or an established cell line, such as an NF-2 inactivated Schwann cell line, can be used.

2. Pharmaceutical Compositions

Aspects also provide pharmaceutical compositions comprising one or more therapeutic agents that are identified by the screening methods provided herein or as are described herein below. Therapeutic agent(s) can be administered to a patient to achieve a therapeutic effect, i.e. useful in modulating LIMK activity and in turn, treating and/or preventing neurofibromatosis or sporadic schwannoma. Pharmaceutical compositions of the invention can comprise, for example, therapeutic agents identified by a screening method embodiment described herein, which are identified by their ability to bind to or affect activity of LIMK polypeptides, or bind to and/or affect expression of LIMK polynucleotides. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other therapeutic agents or treatments.

In addition to the active ingredients, these pharmaceutical compositions can contain suitable pharmaceutically acceptable carriers comprising excipients and auxiliaries which facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the subject.

Further details on techniques for formulation and administration can be found in the latest edition of REMINGTON'S PHARMACEUTICAL SCIENCES (Maack Publishing Co., Easton, Pa., which is incorporated herein by reference). After pharmaceutical compositions have been prepared, they can be placed in an appropriate container and labeled for treatment of an indicated condition. Such labeling would include amount, frequency, and method of administration.

The present invention further pertains to the use of novel agents identified by the screening assays described above. Accordingly, it is within the scope of this invention to use a therapeutic agent identified as described herein in an appropriate animal model. For example, an agent identified as described herein (for example, but not limited to, a modulating agent, an antisense nucleic acid molecule, a specific antibody, ribozyme, interfering molecule, or a LIMK-binding molecule) can be used in an animal model to determine the efficacy, toxicity, or side effects of treatment with such an agent. Furthermore, the present invention includes uses of novel agents identified by the above-described screening assays for treatments as described herein.

Those skilled in the art will appreciate that numerous delivery mechanisms are available for delivering a therapeutic agent to an area of need. By way of example, the agent may be delivered using a liposome as the delivery vehicle. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human.

A liposome useful in the present invention comprises a lipid composition that is capable of fusing with the plasma membrane of the targeted cell to deliver its contents to the cell. Preferably, the transfection efficiency of a liposome is about 0.5 µg of DNA per 16 nmole of liposome delivered to about $1\times10^6$ cells, more preferably about 1.0 µg of DNA per 16 nmole of liposome delivered to about $1\times10^6$ cells, and even more preferably about 2.0 µg of DNA per 16 nmol of liposome delivered to about $1\times10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes conventionally used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

Complexing a liposome with a reagent such as an antisense oligonucleotide or ribozyme can be achieved using methods which are standard in the art (see, for example, U.S. Pat. No. 5,705,151). Preferably, from about 0.1 µg to about 10 µg of polynucleotide is combined with about 8 nmol of liposomes, more preferably from about 0.5 µg to about 5 µg of polynucleotides are combined with about 8 nmol liposomes, and even more preferably about 1.0 µg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. Trends in Biotechnol. 11, 202-05 (1993); Chiou et al., GENE THERAPEUTICS: METHODS AND APPLICATIONS OF DIRECT GENE TRANSFER (J. A. Wolff, ed.) (1994); Wu & Wu, J. Biol. Chem. 263, 621-24 (1988); Wu et al., J. Biol. Chem. 269, 542-46 (1994); Zenke et al., Proc. Natl. Acad. Sci. U.S.A. 87, 3655-59 (1990); Wu et al., J. Biol. Chem. 266, 338-42 (1991).

In one embodiment, the delivery system enhances cell targeting, prolongs circulation time, and/or improves membrane permeation, while being biocompatible and biodegradable. Exemplary delivery systems include lipids, peptides, synthetic and natural polymers, viral and non-viral vectors, liposomes, micelles, emulsions, microemulsions, microtubes, and nanotubes. When the LIMK modulating agent is an siRNA molecule, the delivery system may comprise a regulatory sequence useful in expression constructs/vectors with siRNA. Exemplary regulatory sequences may include a constitutive promoter, an inducible promoter, a tissue-specific promoter, or a combination thereof.

In a particular embodiment, the delivery system comprises a liposome. Liposomes comprising various lipid compositions useful in delivering a LIMK modulating agent as described herein are known in the art. See Fraley, R., and Papahadjopoulos, D., Trends Biochem. Sci. 6: 77-80). Exemplary liposome preparations are available, such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art.

In another embodiment, the delivery of the LIMK modulating agent, typically an interfering molecule, may be accomplished using any one or more of a number of recombinant DNA and gene therapy technologies, including viral vectors. Viral vector methods and protocols are reviewed in Kay et al., Nature Medicine 7:33-40, 2001. Viral vectors useful in the invention include those derived from Adeno-Associated Virus (AAV). An exemplary AAV vector comprises a pair of AAV inverted terminal repeats, which flank at least one cassette containing a promoter which directs expression operably linked to a nucleic acid encoding a molecule that modulates LIMK. Methods for use of recombinant AAV vectors are discussed, for example, in Tal, J., J. Biomed. Sci. 7:279-291, 2000 and Monahan and Samulski, Gene Therapy 7:24-30, 2000.

In a particular embodiment, the LIMK modulating agent may be delivered via using a lentivirus. Lentiviruses are a subclass of retroviruses. They have recently been adapted as gene delivery vehicles (vectors) due to their ability to integrate into the genome of non-dividing cells, which is the unique feature of lentiviruses as other retroviruses may only infect dividing cells. The lentivirus may be particularly suitable for in vivo evaluation of an inhibitor. See e.g., Song Y, Zhang Z, Yu X, Yan M, Zhang X, Gu S, et al. (2006). Application of lentivirus-mediated RNAi in studying gene function in mammalian tooth development. Dev Dyn 235:1334-1344. In yet another embodiment, the delivery system comprises a nanoparticle delivery system such as that disclosed in US Published Patent Application No. 20110091510 (University of Florida Research Foundation), the entirety of which is incorporated by reference.

2.1 Determination of a Therapeutically Effective Dose

The determination of a therapeutically effective dose of therapeutic agents identified by a screening method herein is well within the capability of those skilled in the art. A therapeutically effective dose refers to that amount of active ingredient which modulates LIMK activity compared to that which occurs in the absence of the therapeutically effective dose. Therapeutic efficacy and toxicity, e.g., ED50 (the dose therapeutically effective in 50% of the population) and LD50 (the dose lethal to 50% of the population), can be determined by standard pharmaceutical procedures in cell cultures or experimental animals. The dose ratio of toxic to therapeutic effects is the therapeutic index, and it can be expressed as the ratio, LD50/ED50.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Preferably, a therapeutic agent reduces expression of a LIMK gene or the activity of a LIMK polypeptide by at least about 10, preferably about 50, more preferably about 75, 90, or 100% relative to the absence of the reagent. The effectiveness of the mechanism chosen to decrease the level of expression of a LIMK gene or the activity of a LIMK polypeptide can be assessed such as by hybridization of nucleotide probes to LIMK-specific mRNA, quantitative RT-PCR, immunologic detection of a LIMK polypeptide, or measurement of LIMK activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles.

The combination of therapeutic agents can act synergistically to effect the treatment or prevention of neurofibromatosis or sporadic schwannomas. Using this approach, one may be able to achieve therapeutic efficacy with lower dosages of each agent, thus reducing the potential for adverse side effects. Any of the therapeutic methods described above can be applied to any subject in need of such therapy.

3. Polypeptides

A LIMK polypeptide of the invention therefore can be a portion of a LIMK protein, a full-length LIMK protein, or a fusion protein comprising all or a portion of LIMK protein. In one embodiment, LIMK polypeptides according to the invention comprise at least 12, 15, 25, 50, 75, 100, 125, 150, 175, 200, 225, 250, 300, 350, 400, 450, 500, 525, 550, 575, 600, or 625 contiguous amino acids selected from the amino acid sequence shown in SEQ ID NOS: 1 and 2, or other LIMK sequences disclosed above or known in the art, or a biologically active variant thereof, as defined below.

3.1 Biologically Active Variants

LIMK polypeptide variants which are biologically active also are considered LIMK polypeptides for purposes of this application. In one embodiment, naturally or non-naturally occurring LIMK polypeptide variants have amino acid sequences which are at least about 55, 60, 65, or 70, preferably about 75, 80, 85, 90, 96, 96, or 98% identical to the amino acid sequence shown in SEQ ID NOS: 1 and 2, or other LIMK sequences disclosed above or known in the art, or a fragment thereof. Percent identity between a putative LIMK polypeptide variant and an amino acid sequence for LIMK may be determined using the Blast2 alignment program (Blosum62, Expect 10, standard genetic codes).

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of a LIMK polypeptide can be found using computer programs well known in the art, such as DNASTAR software. Whether an amino acid change results in a biologically active LIMK polypeptide can readily be determined by assaying for LIMK activity as would be readily determined by one skilled in the art.

3.2 Fusion Proteins

In some embodiments of the invention, it is useful to create fusion proteins. By way of example, fusion proteins are useful for generating antibodies against LIMK polypeptide amino acid sequences and for use in various assay systems. For example, fusion proteins can be used to identify proteins which interact with portions of a LIMK polypeptide. Protein affinity chromatography or library-based assays for protein—protein interactions, such as the yeast two-hybrid or phage display systems, can be used for this purpose. Such methods are well known in the art and also can be used as drug screens.

A LIMK polypeptide fusion protein comprises two polypeptide segments fused together by means of a peptide bond. For example, the first polypeptide segment can comprise at least 12, 15, 25, 50, 75, 100, 125, 150, 175, 200, 225, or 250 contiguous amino acids of SEQ ID NOS: 1 and 2, or other LIMK sequence referenced above or known in the art. The first polypeptide segment also can comprise full-length LIMK protein. The second polypeptide segment can be a full-length protein or a protein fragment. Proteins commonly used in fusion protein construction include galactosidase, glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP 16 protein fusions. A fusion protein also can be engineered to contain a cleavage site located between the LIMK polypeptide-encoding sequence and the heterologous protein sequence, so that the LIMK polypeptide can be cleaved and purified away from the heterologous moiety.

Numerous different kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

4. Polynucleotides

A LIMK polynucleotide can be single- or double-stranded and comprises a coding sequence or the complement of a coding sequence for a LIMK polypeptide. A coding sequence for the LIMK polypeptides, such as those disclosed by SEQ ID NOS: 1 and 2 are readily ascertainable by one skilled in the art. Degenerate nucleotide sequences encoding LIMK polypeptides, as well as homologous nucleotide sequences which are at least about 50, 55, 60, 65, 60, preferably about 75, 90, 96, or 98% identical to a particular LIMK nucleotide sequence are also LIMK-like enzyme polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of LIMK polynucleotides which encode biologically active LIMK polypeptides also are LIMK polynucleotides.

4.1 Identification of Polynucleotide Variants and Homologs

Variants and homologs of the LIMK polynucleotides described above also are LIMK polynucleotides. Typically, homologous LIMK polynucleotide sequences can be identified by hybridization of candidate polynucleotides to known LIMK polynucleotides under stringent conditions, as is known in the art. For example, using the following wash conditions: 2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each homologous sequences can be identified which contain at most about 25-30% basepair mismatches. More preferably, homologous nucleic acid strands contain 15-25% basepair mismatches, even more preferably 5-15% basepair mismatches.

Species homologs of the LIMK polynucleotides disclosed herein also can be identified by making suitable probes or primers and screening cDNA expression libraries. It is well known that the Tm of a double-stranded DNA decreases by 1-1.5° C. with every 1% decrease in homology (Bonner et al, J. Mol. Biol. 81, 123 (1973). Variants of LIMK polynucleotides or polynucleotides of other species can therefore be identified by hybridizing a putative homologous LIMK polynucleotide with a polynucleotide having a LIMK nucleotide sequence or complement thereof to form a test hybrid. The melting temperature of the test hybrid is compared with the melting temperature of a hybrid comprising polynucleotides having perfectly complementary nucleotide sequences, and the number or percent of basepair mismatches within the test hybrid is calculated.

Nucleotide sequences which hybridize to LIMK polynucleotides or their complements following stringent hybridization and/or wash conditions also are LIMK polynucleotides. Stringent wash conditions are well known and understood in the art and are disclosed, for example, in Sambrook et al., MOLECULAR CLONING: A LABORATORY MANUAL, 2 nd ed., 1989, at pages 9.50-9.51.

Typically, for stringent hybridization conditions a combination of temperature and salt concentration should be chosen that is approximately 12-20° C. below the calculated Tm (melting temperature) of the hybrid under study. The $T_m$ of a hybrid between a LIMK polynucleotide or a complement thereof and a polynucleotide sequence which is at least about 50, preferably about 75, 90, 96, or 98% identical to one of those nucleotide sequences can be calculated, for example, using the equation of Bolton and McCarthy, Proc. Natl. Acad. Sci. U.S.A. 48, 1390 (1962):

$T_m=81.5°$ C.$-16.6(\log_{10}[Na+])+0.41(\%$ G+C$)-0.63(\%$ formamide$)-600/1)$, where 1=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

4.2 Preparation of Polynucleotides

A naturally occurring LIMK polynucleotide can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated LIMK polynucleotides. For example, restriction enzymes and probes can be used to isolate polynucleotide fragments, which comprise LIMK nucleotide sequences. Isolated polynucleotides are in preparations which are free or at least 70, 80, or 90% free of other molecules.

LIMK DNA molecules can be made with standard molecular biology techniques, using LIMK mRNA as a template. LIMK DNA molecules can thereafter be replicated using molecular biology techniques known in the art and disclosed in manuals such as Sambrook et al. (1989). An amplification technique, such as PCR, can be used to obtain additional copies of polynucleotides of the invention. The inventors have successfully demonstrated this approach.

Alternatively, synthetic chemistry techniques can be used to synthesize LIMK polynucleotides. The degeneracy of the genetic code allows alternate nucleotide sequences to be synthesized which will encode a LIMK polypeptide or a biologically active variant thereof.

4.3 Expression of Polynucleotides

To express a LIMK polynucleotide, the polynucleotide can be inserted into an expression vector which contains the necessary elements for the transcription and translation of the inserted coding sequence. Methods which are well known to those skilled in the art can be used to construct expression vectors containing sequences encoding LIMK polypeptides and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., CURRENT PROTOCOLS IN MOLECULAR BIOLOGY, John Wiley & Sons, N. Y., N.Y., 1989.

A variety of expression vector/host systems can be utilized to contain and express sequences encoding a LIMK polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those nontranslated regions of the vector enhancers, promoters, 5' and 3' untranslated regions which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding a LIMK polypeptide, vectors based on SV40 or EBV can be used with an appropriate selectable marker.

5. Host Cells

According to certain embodiments of the subject invention, a LIMK polynucleotide will need to be inserted into a host cell, for expression, processing and/or screening. A host cell strain can be chosen for its ability to modulate the expression of the inserted sequences or to process the expressed LIMK polypeptide in the desired fashion. Such modifications of the polypeptide include, but are not limited to, acetylation, carboxylation, glycosylation, phosphorylation, lipidation, and acylation. Posttranslational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; 10801 University Boulevard, Manassas, Va. 20110-2209) and can be chosen to ensure the correct modification and processing of the foreign protein.

Stable expression is preferred for long-term, high yield production of recombinant proteins. For example, cell lines which stably express LIMK polypeptides can be transformed using expression vectors which can contain viral origins of replication and/or endogenous expression elements and a selectable marker gene on the same or on a separate vector. Following the introduction of the vector, cells can be allowed to grow for 12 days in an enriched medium before they are switched to a selective medium. The purpose of the selectable marker is to confer resistance to selection, and its presence allows growth and recovery of cells which successfully express the introduced LIMK sequences. Resistant clones of stably transformed cells can be proliferated using tissue culture techniques appropriate to the cell type. See, for example, ANIMAL CELL CULTURE, R. I. Freshney, ed., 1986.

5.1 Detecting Expression

A variety of protocols for detecting and measuring the expression of a LIMK polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a LIMK polypeptide can be used, or a competitive binding assay can be employed. These and other assays are described in Hampton et al, SEROLOGICAL METHODS: A LABORATORY MANUAL, APS Press, St. Paul, Minn., 1990) and Maddox et al., J. Exp. Med. 158, 12111216, 1983).

5.2 Expression and Purification of Polypeptides

Host cells transformed with nucleotide sequences encoding LIMK polypeptide can be cultured under conditions suitable for the expression and recovery of the protein from cell culture. The polypeptide produced by a transformed cell can be secreted or contained intracellular depending on the sequence and/or the vector used. As will be understood by those of skill in the art, expression vectors containing polynucleotides which encode LIMK polypeptides can be designed to contain signal sequences which direct secretion of soluble LIMK polypeptides through a prokaryotic or eukaryotic cell membrane or which direct the membrane insertion of membrane-bound LIMK polypeptide.

6. Antibodies

Antibodies are referenced herein and various aspects of the subject invention utilize antibodies specific to LIMK polypeptide(s). As described above, one example of a therapeutic agent for inhibiting LIMK may pertain to an antibody. Any type of antibody known in the art can be generated to bind specifically to an epitope of a LIMK polypeptide. The term "antibody" as used herein includes intact immunoglobulin molecules, as well as fragments thereof, such as Fab, F(ab') 2, and Fv, which are capable of binding an epitope of a LIMK polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of a LIMK polypeptide can be used therapeutically, as mentioned, as well as in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen. Antibodies useful for embodiments of the subject invention may be polyclonal, but are preferably monoclonal antibodies.

7. Ribozymes

Ribozymes may be one category of test compounds potentially useful as therapeutic agents for modulating LIMK activity. Ribozymes are RNA molecules with catalytic activity. See, e.g., Cech, Science 236, 15321539; 1987; Cech, Ann. Rev. Biochem. 59, 543568; 1990, Cech, Curr. Opin. Struct. Biol. 2, 605609; 1992, Couture & Stinchcomb, Trends Genet. 12, 510515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

Accordingly, another aspect of the invention pertains to using the coding sequence of a LIMK polynucleotide to generate ribozymes which will specifically bind to mRNA transcribed from the LIMK polynucleotide. Methods of designing and constructing ribozymes which can cleave other RNA molecules in trans in a highly sequence specific manner have been developed and described in the art (see Haseloff et al. Nature 334, 585591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within a LIMK RNA target can be identified by scanning the target molecule for ribozyme cleavage sites. Once identified, short RNA sequences of between 15 and 20 ribonucleotides corresponding to the region of the target RNA containing the cleavage site can be evaluated for secondary structural features which may render the target inoperable. Suitability of candidate LIMK RNA targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease LIMK expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors which induce expression of a target gene. Ribozymes also can be engineered to provide an additional level of regulation, so that destruction of mRNA occurs only when both a ribozyme and a target gene are induced in the cells. Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989); Methods in Plant Molecular Biology, Maliga et al, Eds., Cold Spring Harbor Laboratory Press, New York (1995); *Arabidopsis*, Meyerowitz et al, Eds., Cold Spring Harbor Laboratory Press, New York (1994) and the various references cited therein.

8. Interfering Molecules

LIMK can be inhibited by a number of means including silencing via miRNA, shRNA, or siRNA, for example, directed to a portion of the sequence described at the genbank accession numbers provided herein. In one embodiment, the LIMK modulating agent comprises an interfering molecule, and wherein the interfering molecule comprises a member selected from the group consisting of a phosphothioate morpholino oligomer (PMO), miRNA, siRNA, methylated siRNA, treated siRNAs, shRNA, antisense RNA, a dicer-substrate 27-mer duplex, and combinations thereof.

siRNA molecules can be prepared against a portion of a nucleotide sequence encoding LIMK according to the techniques provided in U.S Patent Publication 20060110440, incorporated by reference herein, and used as therapeutic compounds. shRNA constructs are typically made from one of three possible methods; (i) annealed complementary oligonucleotides, (ii) promoter based PCR or (iii) primer extension. See Design and cloning strategies for constructing shRNA expression vectors, Glen J McIntyre, Gregory C FanningBMC Biotechnology 2006, 6:1 (5 Jan. 2006).

For background information on the preparation of miRNA molecules, see e.g. U.S. patent applications 20110020816, 2007/0099196; 2007/0099193; 2007/0009915; 2006/0130176; 2005/0277139; 2005/0075492; and 2004/0053411, the disclosures of which are hereby incorporated by reference herein. See also, U.S. Pat. Nos. 7,056,704 and 7,078,196 (preparation of miRNA molecules), incorporated by reference herein. Synthetic miRNAs are described in Vatolin, et al 2006 J Mol Biol 358, 983-6 and Tsuda, et al 2005 Int J Oncol 27, 1299-306, incorporated by reference herein. See also U.S. patent applications 20120034236 and 20110251255, incorporated by reference herein, for further examples of interfering molecules for targeting LIMK expression, for example.

9. Small Molecules

Small molecules compounds for inhibiting LIMK activity or proliferation may be identified by the screening methods described herein. In addition, the present inventors have found that the compound BMS-5 reduced cofilin phosphorylation in mouse Schwann cells. In accordance with one aspect, the LIMK modulating agent comprises BMS5 or a derivative, analog, or prodrug thereof. The present inventors found that BMS-5 inhibited proliferation of mouse-inactivated Schwannoma Cells (NF2-MTC cells) under various inhibitor concentrations. In accordance with another aspect, the LIMK modulating agent comprises BMS-5, alone or in combination with other LIMK modulating agents, or other inhibitors or chemotherapies. The structure of BMS-5 is provided below:

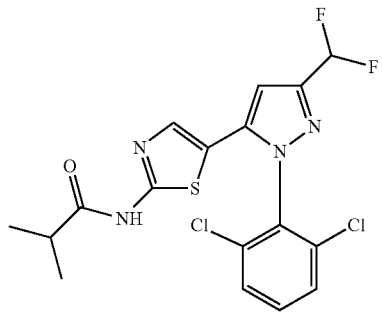

N-(5-(1-(2,6-dichlorophenyl)-3-(difluoromethyl)-1H-pyrazol-5-yl)thiazol-2-yl)isobutyramide In another aspect, the LIMK modulating agent comprises TAK165, Rapamycin, or a combination thereof. TAK165 has been identified as a Novel HER2 selective tyrosine kinase inhibitor. Rapamycin (also known as Sirolimus) is an immunosuppressant drug typically used to prevent rejection in organ transplantation.

Additional small molecule inhibitors are set forth and described in WO 2006084017 and EP 2297153 A1, the entirety of each of which is incorporated by reference herein. Further LIMK modulating agents are disclosed in Manetti, F., *LIM Kinases Are Attractive Targets with Many Macromolecular Partners and Only a Few Small Molecule Regulators*, published online in Wiley Online Library (wileyonlinelibrary.com), DOI 10.1002/med.20230; Ross-McDonald, P., de Silva, H., Guo, Q., Xiao, H., Hung, C., Penhallow, B., Markwalder, J., He, L., Attar, R., Lin, T., Seitz, S. Tifford, C., Wardwell-Swanson, J., Jackson, D., Identification of a non-kinase target mediating cytotoxicity of novel kinase inhibitors, Mol Cancer Ther 2008:7(11). November 2008.

10. Other Modulators and High Throughput Techniques

A. Modulators

The compounds tested as modulators of a LIMK can be any small chemical compound, or a biological entity, such as a protein, sugar, nucleic acid or lipid. Typically, test compounds will be small chemical molecules and peptides. Essentially any chemical compound can be used as a potential modulator in the assays of the invention. The compounds can be dissolved in aqueous or organic solutions (e.g., methanol, DMSO, or a mixture of organic solvents). The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In one embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

B. Solid State and Soluble High Throughput Assays

In one embodiment the invention provides in vitro soluble assays in a high throughput format. In another embodiment, the invention provides soluble or solid phase based in vivo assays in a high throughput format, where the cell or tissue is attached to a solid phase substrate. Optionally, the in vitro assay is a solid phase assay.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100- about 1500 different compounds. It is possible to assay several different plates per day; assay screens for up to about 6,000-20,000 different compounds are possible using the integrated systems of the invention. More recently, microfluidic approaches to reagent manipulation have been developed.

The molecule or cell of interest can be bound to the solid state component, directly or indirectly, via covalent or non-covalent linkage of a tag and or a tag binder. A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and appropriate tag binders; see SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface, which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

C. Labels and Means of Detection

Detectable labels and moieties can be primary labels (where the label comprises an element which is detected directly or which produces a directly detectable element) or secondary labels (where the detected label binds to a primary label, e.g., as is common in immunological labeling). An introduction to labels, labeling procedures and detection of labels is found in Polak & Van Noorden (1997) *Introduction to Immunocytochemistry* (2$^{nd}$ ed. 1977) and *Handbook of Fluorescent Probes and Research Chemicals*, a combined handbook and catalogue Published by Molecular Probes, Inc., Eugene, Oreg. Primary and secondary labels can include undetected elements as well as detected elements.

The particular label or detectable group used in the assay is not a critical aspect of the invention, as long as it does not significantly interfere with the specific binding of an agent used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means.

Useful primary and secondary labels in the present invention can include spectral labels such as fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P, etc.), enzymes (e.g., horseradish peroxidase, alkaline phosphatase etc.), spectral colorimetric labels such as colloidal gold or colored glass or plastic (e.g. polystyrene, polypropylene, latex, etc.) beads.

The label may be coupled directly or indirectly to a component of the detection assay according to methods well known in the art. Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. As indicated above, a wide variety of labels may be used, with the choice of label depending on sensitivity required, ease of conjugation with the compound, stability requirements, available instrumentation, and disposal provisions.

In general, a detector that monitors a particular probe or probe combination is used to detect the recognition reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling nucleic acids is digitized for subsequent computer analysis.

Preferred labels include those which utilize enzymes such as hydrolases, particularly phosphatases, kinases, esterases and glycosidases, or oxidotases, particularly peroxidases; chemiluminescence (e.g., enzymes such as horseradish peroxidase or alkaline phosphatase with substrates that produce photons as breakdown products; kits available, e.g., from Molecular Probes, Amersham, Boehringer-Mannheim, and Life Technologies/Gibco BRL); color production (using, e.g., horseradish peroxidase, β-galactosidase, or alkaline phosphatase with substrates that produce a colored precipitate; kits available from Life Technologies/Gibco BRL, and Boehringer-Mannheim); hemifluorescence (using, e.g., alkaline phosphatase and the substrate AttoPhos (Amersham) or other substrates that produce fluorescent products); fluorescence (e.g., using Cy-5 (Amersham), fluorescein, and other fluorescent tags, and fluorescent proteins such as Green and Red Fluorescent Protein); antibodies bound to a detectable moiety, and radioactivity. Other methods for labeling and detection will be readily apparent to one skilled in the art. For example, phenotypic changes such as drug resistance can be used as a "label" in the present invention.

Typical enzymes that can be used as reporters or detectable moieties include, e.g., β-galactosidase, luciferase, green or red fluorescent protein, kinase, peroxidase, e.g., horse radish peroxidase, phosphatase, e.g., alkaline phosphatase, and chloramphenicol transferase. The chemiluminescent substrate for luciferase is luciferin. One embodiment of a chemiluminescent substrate for β-galactosidase is 4-methylumbelliferyl-β-D-galactoside. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl) spiro[1,2-dioxetane-3,2'-adamantane], which is detected with a luminometer. Embodiments of horse radish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which are detected with a spectrophotometer; and 3,3,5,5'-tetramethylbenzidine (TMB), 3,3'diaminobenzidine (DAB), 3-amino-9-ethylcarbazole (AEC), and 4-chloro-1-naphthol (4C1N), which are detected visually. Other suitable substrates are known to those skilled in the art. The enzyme-substrate reaction and product detection are performed according to standard procedures known to those skilled in the art and kits for performing enzyme immunoassays are available as described above.

RNA expression can also analyzed by techniques known in the art, e.g., reverse transcription and amplification of mRNA, e.g., RTQ-PCR, isolation of total RNA or poly A+ RNA, northern blotting, dot blotting, in situ hybridization, RNase protection, probing DNA microchip arrays, and the like. In one embodiment, high density oligonucleotide analysis technology (e.g., GeneChip™) is used to identify reporter RNA molecules of the invention, see, e.g., Gunthand et al., *AIDS Res. Hum. Retroviruses* 14: 869-876 (1998); Kozal et al., *Nat. Med.* 2:753-759 (1996); Matson et al., *Anal. Biochem.* 224: 110-106 (1995); Lockhart et al., *Nat. Biotechnol.* 14:1675-1680 (1996); Gingeras et al., *Genome Res.* 8:435-448 (1998); Hacia et al., *Nucleic Acids Res.* 26:3865-3866 (1998).

EXAMPLES

Referring to FIG. 1, testing showed that BMS-5 reduces the phosphorylation level of cofilin, the substrate for LIMK. Results from dose response experiments indicate that BMS-5 reduces the amount of cofilin phosphorylation in normal rate Schwann cells. Accordingly, the drug affects the reported target and the amount needed to reduce cofilin phosphorylation by 50% of the untreated control is 0.2 µm BMS-5.

Figure 2:
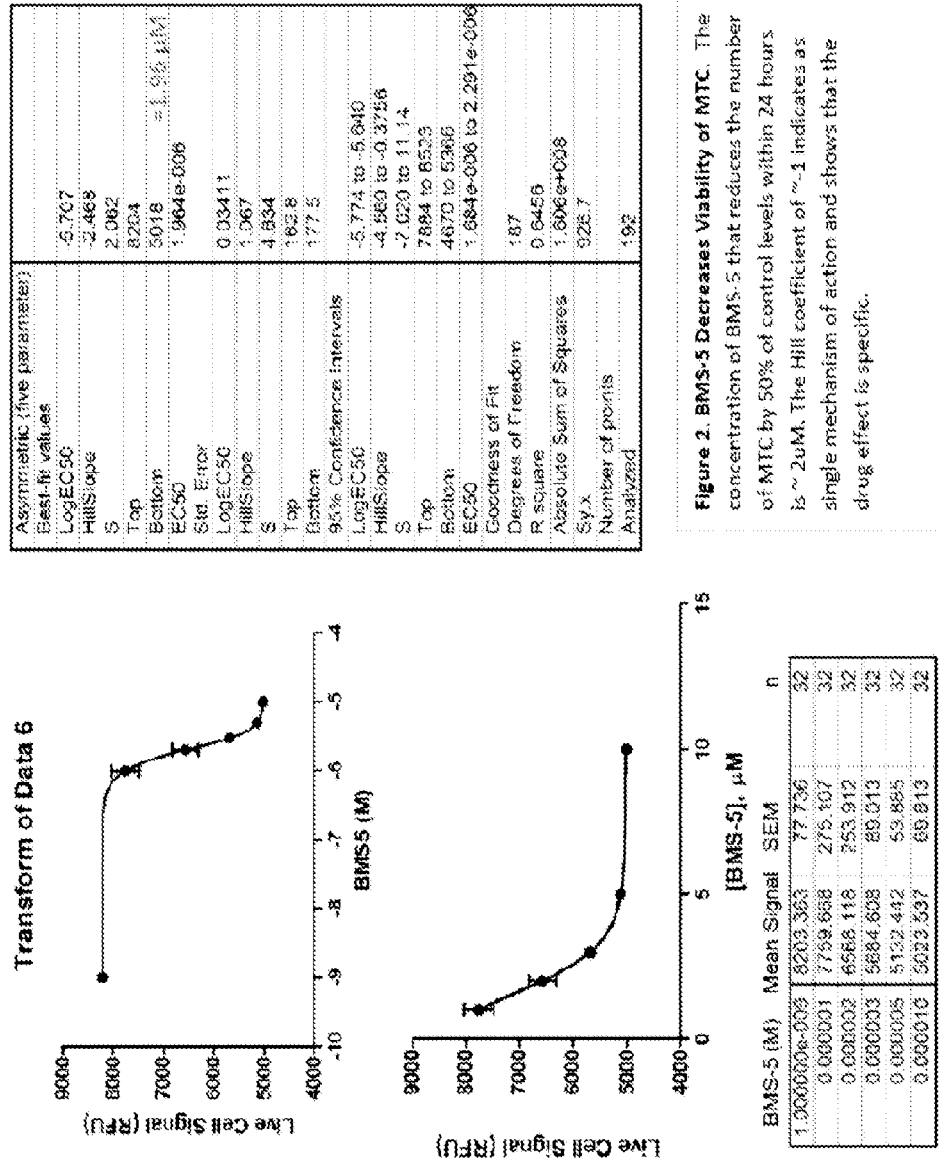
FIG. 2. BMS-5 Decreases Viability of Mouse Merlin-Null Schwann Cells. The concentration of BMS-5 that reduces the number of mouse merlin-null Schwann cells by 50% of control levels within 24 hours is approximately 2 µm. The Hill coefficient of about 1 indicates a single mechanism of action and shows that the drug effect is specific.

FIG. 2 shows proliferation of mouse NF-2 inactivated Schwannoma Cells (hereinafter "NF2-MTC"). NF2 was tested in the presence of increasing concentration of BMS-5 in a 96-well format (32 replicates/concentrations) using a commercially available cell viability assay (Promega-Multi-tox-Fluor). The number of MTC present after 24 hours of growth in the presence of BMS-5 was measured. The results indicate that there is dose-respondent inhibition of MTC number. The $EC_{50}$ was determined to be 1.96 µm with a Hill slope equal to −1.067 indicative of a single mechanism of action. The results indicate that BMC-5 either kills the MTC's or inhibits their proliferation.

Figure 3:
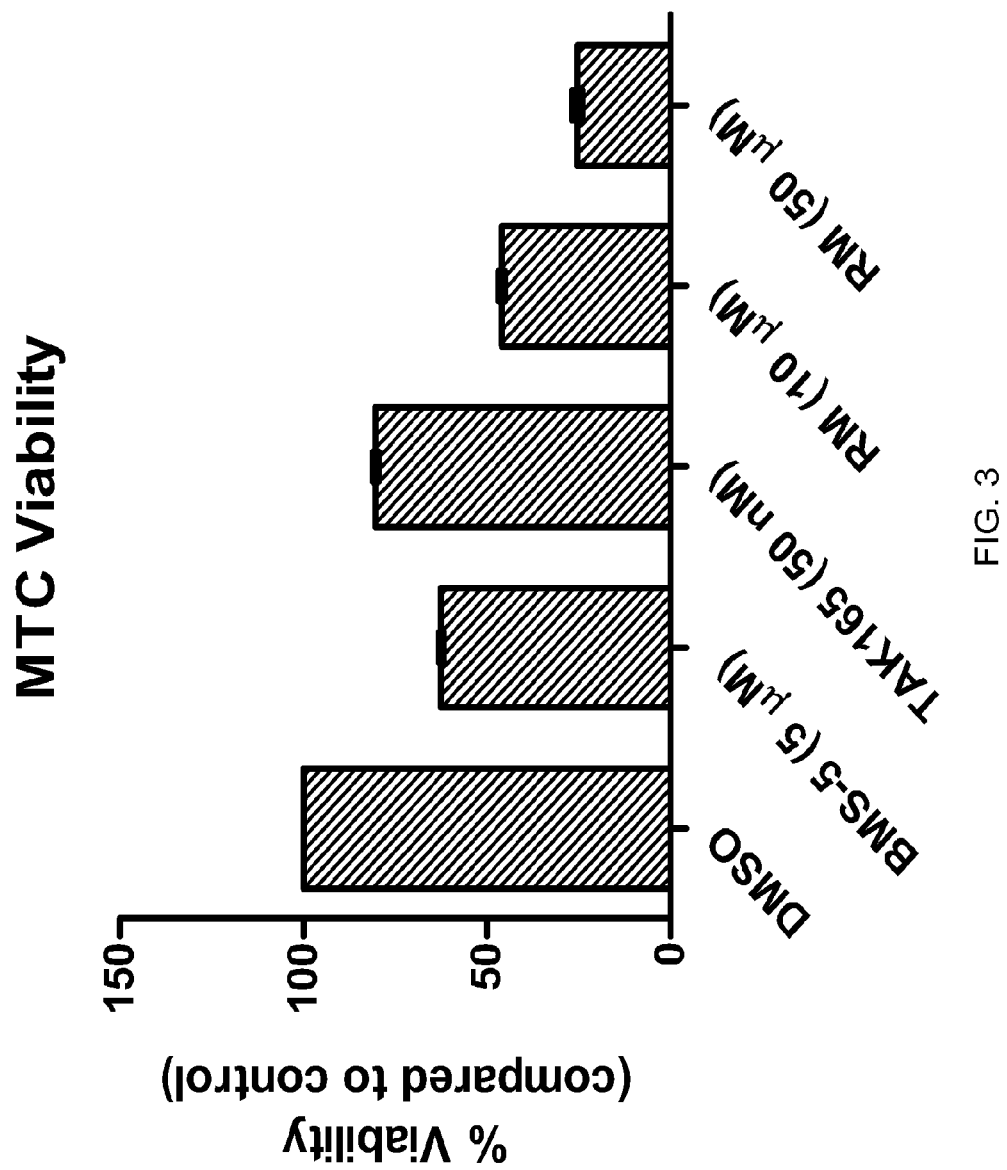
FIG. 3. Comparative Effect of BMS-5 in Reducing Mouse merlin-null Schwan Cell Viability. The result of a 24 hour viability assay of mouse merlin null Schwann cells grown in the presence of BMS-5 and other compounds under development for NF2 by others is shown. The study shows that BMS-5 causes a 40% reduction in the viability of merlin-null Schwann cells and is comparable to rapamycin.

Referring to FIG. 3, the effectiveness of BMS-5 with two other compounds was measured. A viability assay was described in FIG. 2 and compared the ability of BMS-5 (5 µM), TAK 165 (50 nM) and rapamycin (10 and 50 µM) to decrease MTC viability as measured with the Multi-tox-Fluor assay (FIG. 3). The results demonstrate that BMS-5 at the tested dose reduced MTC viability compared to the DMSO (untreated) control. The other drugs served as positive controls and also were effective in reducing MTC viability. This result shows that our assay effectively measures viability and that BMS-5 is a promising drug.

Figure 4:
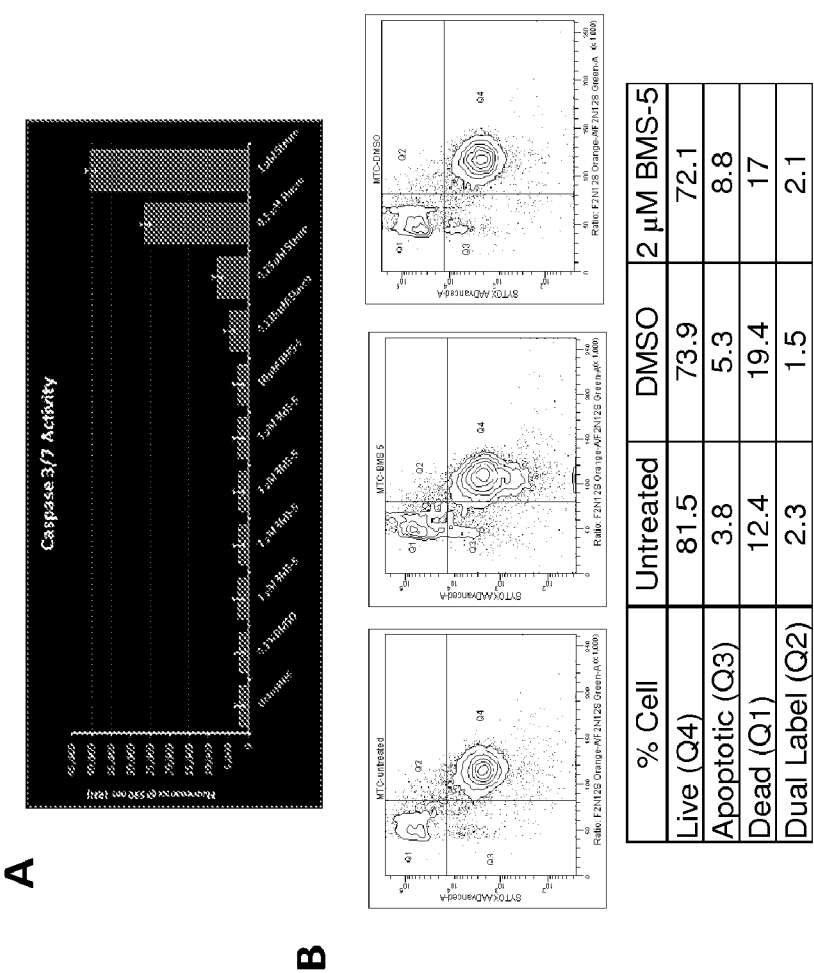
FIGS. 4A-B. BMS-5 Induction of Apoptotic Cell Death Routine is not the Primary Mechanism of Decrease in Mouse Merlin-Null Schwann Cells Viability. A) BMS-5 does not reduce cell viability by inducing caspase dependent apoptosis. The study of caspase 3/7 activity after 8 hours incubation with the drugs shows no significant difference in the caspase activity of untreated or DMSO controls and the increasing doses of BMS-5, while a recognized apoptotic induingr agent Staurosporine does. B) Incubation of mouse Merlin-null Schwann cells with 2 µM BMS-5 for 24 hours does not significantly increase the number of cells with plasma membrane asymmetry, characteristic of all subroutines of apoptotic cell death.

Referring to FIG. 4, BMS-5 Induction of Apoptotic Cell Death Routine is not the Primary Mechanism of Decrease in Mouse Merlin-Null Schwann Cells Viability. BMS-5 was shown not to reduce cell viability by inducing caspase dependant apoptosis. A study of caspase 3/7 activity after 8 hours incubation with the drugs shows no significant difference in the caspase activity of untreated or DMSO controls and the increasing doses of BMS-5, while a recognized apoptotic inducer agent Staurosporine does. Moreover, incubation of mouse Merlin-null Schwann cells with 2 µM BMS-5 for 24 hours does not significantly increase the number of cells with plasma membrane asymmetry, characteristic of all subroutines of apoptotic cell death.

Figure 5:
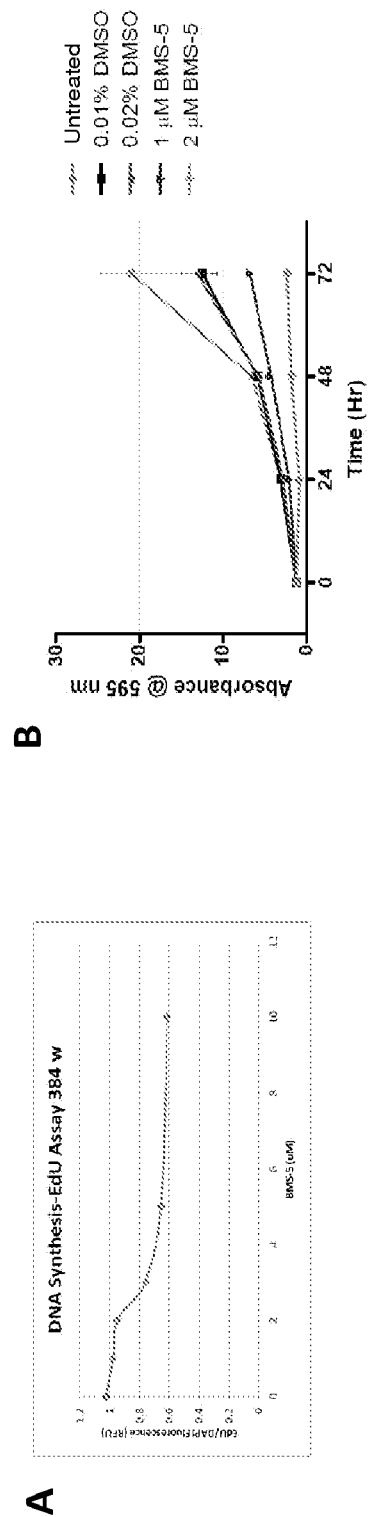
FIGS. 5A-B. BMS-5 Reduces the Proliferation Rate of Mouse Merlin-Null Schwann Cells. A) The result of a 24 hour EdU cell proliferation assay of mouse merlin-null Schwann cells grown in the presence of increasing concentrations of BMS-5 shows a dose dependent decrease of the number of cell with active DNA synthesis. In the study, 10 µM BMS-5 decreased in a 40% the rate of DNA synthesis. This proves that BMS-5 decrease mouse merlin-null Schwann cells viability by hindering cell proliferation. B) A 72 hours treatment with 1 and 2 µM BMS-5 and evaluation of cell number with the Crystal Violet assay showed a decrease in the cell number compared to the untreated of DMSO controls. 2 µM BMS-5 treatment showed no change in the number of mouse merlin-null Schwann cells after 72 hours.

Referring to FIG. 5, BMS-5 Reduces the Proliferation Rate of Mouse Merlin-Null Schwann Cells. The result of a 24 hour EdU cell proliferation assay of mouse merlin-null Schwann cells grown in the presence of increasing concentrations of BMS-5 showed a dose dependent decrease of the number of cell with active DNA synthesis. Moreover, a 10 µM BMS-5 decreased in a 40% the rate of DNA synthesis. This proves that BMS-5 decrease mouse merlin-null Schwann cells viability by hindering cell proliferation. A 72 hours treatment with 1 and 2 µM BMS-5 and evaluation of cell number with the Crystal Violet assay showed a decrease in the cell number compared to the untreated of DMSO controls. 2 µM BMS-5 treatment showed no change in the number of mouse merlin-null Schwann cells after 72 hours.

Figure 6:
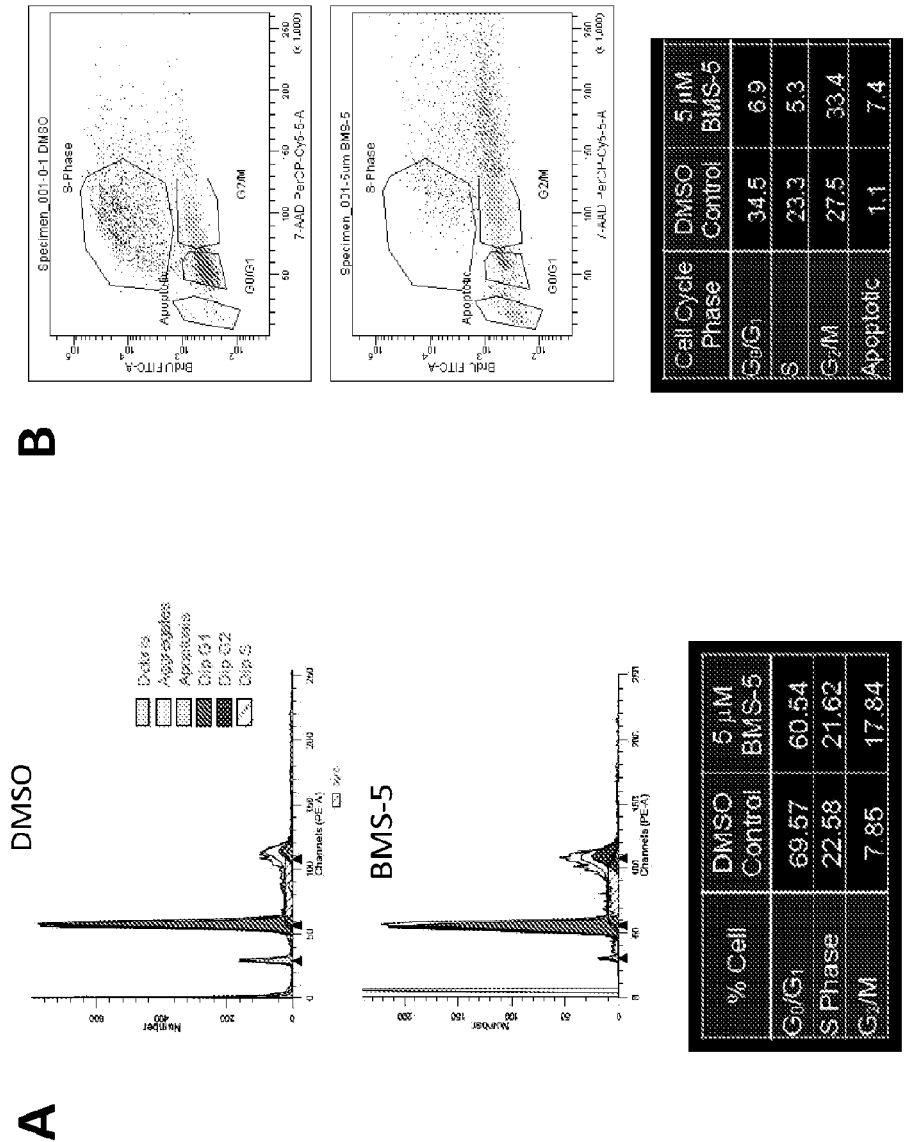
FIGS. 6A-6B. BMS-5 Increases the Number of Mouse Merlin-Null Schwann Cells in the $G_2/M$ phase of the Cell Cycle. A) A flow cytometry assay with mouse merlin-null Schwann cells treated for 17 hr with 5 µM BMS-5 then stained with Propidium Iodine showed that cell in $G_2/M$ phase increased in more than 100%. B) Analysis of BrdU/7-AAD assay by flow cytometry of mouse merlin-null Schwann cells treated for 24 hr with 5 µM BMS-5 and incubated for the last 3 hr with BrdU showed a moderate increase in the number of cell in $G_2/M$. A massive depletion of cells in $G_0/G_1$ and S phase without an equivalent increase in dead cells indicate that great part of the BMS-5 treated cell population is unable to divide after DNA synthesis.

Referring to FIG. 6, BMS-5 was shown to increase the number of Mouse Merlin-Null Schwann Cells in the $G_2/M$ phase of the Cell Cycle. A flow cytometry assay with mouse merlin-null Schwann cells treated for 17 hr with 5 µM BMS-5 then stained with Propidium Iodine showed that cell in $G_2/M$ phase increased in more than 100%. Analysis of BrdU/7-AAD assay by flow cytometry of mouse merlin-null Schwann cells treated for 24 hr with 5 µM BMS-5 and incubated for the last 3 hr with BrdU showed a moderately increase of cell in $G_2/M$. A massive depletion of cells in $G_0/G_1$ and S phase without an equivalent increase in dead cells indicate that great part of the BMS-5 treated cell population is unable to divide after mitosis.

11. Merlin-Specific Chemical Compounds

Figure 7:
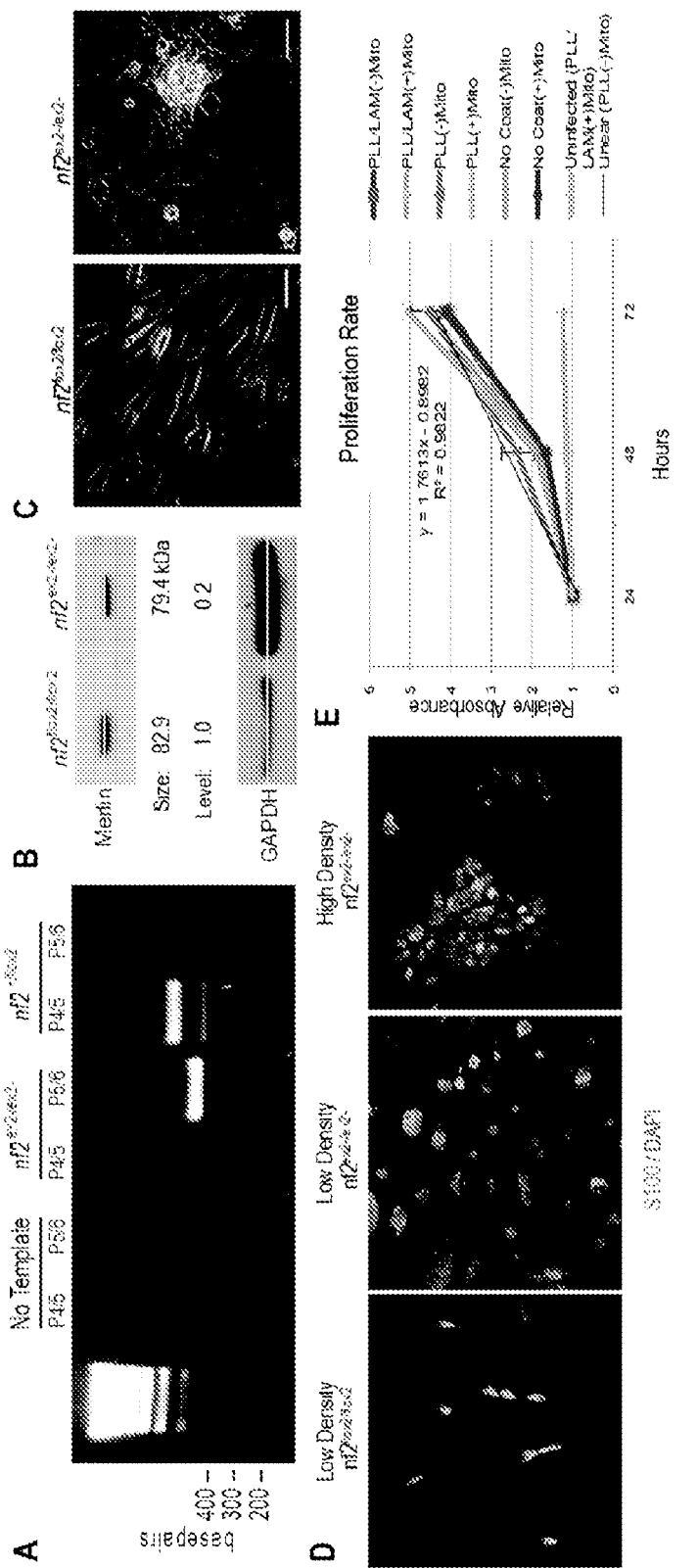
FIGS. 7A-E: Creation and Characterization of Merlin-Null Mouse Schwann Cells. A) PCR amplification with primer set P5/6 produces a 338 bp band indicative of loss of nf2 exon2, while amplification with primer set P4/5 produces 305 bp and 442 bp bands indicative of a wild-type allele and floxed allele, respectively. B) Merlin protein expressed by mouse Schwann cells (nf2$^{ex2-/-}$) has the expected size decrease (~40 amino acid deletion) and its expression level nf2$^{ex2-/-}$ relative to uninfected mouse Schwann cells nf2$^{flox2/flox2}$ is reduced by 80%. C) Phenotype of nf2$^{flox2/flox2}$ and nf2$^{ex2-/-}$ at high density. (D) S 100, a Schwann cell marker is expressed by nf2$^{ex2-/-}$ cells; these cells are larger than controls and are round rather than bipolar. nf2$^{ex2-/-}$ cells grown in the absence of mitogens and laminin proliferate faster than nf2$^{flox2/flox2}$ grown in the presence of mitogens and laminin.

Referring to FIG. 7, in accordance with another aspect, there is provided a novel Merlin-null Schwann cell model that proliferates rapidly and is reflective of the disease phenotype. To validate the use of the Merlin-null Schwann cells in an established screening platform, the present inventors successfully conducted a pilot screen of Sigma-Aldrich's Library of Pharmaceutically Active Compounds (LOPAC). This screen identified a number of compounds that modulate known Merlin-dependent pathways. In this way, these compounds could potentially jump-start development of novel therapeutic compounds for schwannomas and other tumors with Merlin inactivation.

Merlin-specific chemical compounds have not been identified in part because of the difficulty in assessing the active versus inactive tumor suppressor, the many signaling pathways it influences, and the lack of a suitable cell line that is Merlin-deficient, cell-type relevant and easy to grow. The major innovative aspect of this proposal is the unique Merlin-null Schwann cell line we created from primary Schwann cells isolated from sciatic nerves of nf2flox2/flox2 mice[19]. These Merlin-null Schwann cells grow rapidly making them suitable for high throughput screening assays. Importantly, they retain expression of Schwann cell markers and phenotypically model human schwannoma cells. This is a major accomplishment given the inherent difficulty in preparing and cultivating primary mouse Schwann cells. An additional innovative aspect is the application of an unbiased chemical biology approach to identification of novel reagents that will be available to the research community. This approach has the potential of uncovering unknown pathways that will open new avenues of research in neurofibromatosis. A further innovation is the likely therapeutic value of the compounds for NF2 and other sporadically occurring tumors arising from Merlin inactivation. A still further innovation is the potential relevance of the compounds to cancer and developmental biology due to merlin's role in the MST-YAP pathway. In 2006, Merlin was shown to regulate Hippo (the MST homolog) in *Drosophila* to promote proliferation arrest and apoptosis of imaginal disc cells[20]. Since then, this pathway has been found to control mammalian tissue homeostasis including organ size and oncogenesis[21-23]. Therefore, Merlin compounds are likely to impact broad areas of basic and translational beyond Schwann cell biology and NF2.

11.1 Creation and Characterization of Merlin-Null Nf2$^{ex2-/-}$ Mouse Schwann Cells To establish a novel Merlin-null Schwann cell model amenable to HTS campaigns, the present inventors used the sole mouse model for NF2 that replicates a documented mutation in humans, in-frame deletion of exon 2[19]. Nf2 exon 2 is flanked with LoxP sequences to allow in vitro adeno-Cre mediated deletion of exon 2. The mutant protein lacks 40 amino acids, 20 of which encode a paxillin binding-domain identified by the PI. This domain is necessary for its translocation to the plasma membrane, serine518 phosphorylation, and association with β1 integrin and ErbB2 receptors[24-26]. In the absence of this domain, merlin is rapidly degraded in the proteasome and the cells are functionally "Merlin-null"[27]. Schwann cells were isolated from sciatic nerves of 3-6 week-old homozygous nf2$^{flox2/flox2}$ mice. The primary nf2$^{flox2/flox2}$ Schwann cells were purified and expanded for two passages and then were transduced with Adeno-Cre virus. The transduced cell population was expanded and deletion of nf2 exon 2 was verified by PCR analysis of genomic DNA and Merlin western blots (FIG. 7A, B).

The Merlin-null Schwann cells morphologically resembled human schwannoma cells in the loss of their phenotypic bipolar morphology and altered growth characteristics. Whereas normal mouse Schwann cells grow only on a poly-L-lysine and laminin substrate in serum-free medium supplemented with forskolin and neuregulin, the Merlin-null Schwann cells grow on uncoated plastic in the absence of serum, forskolin and neuregulin. Unlike primary mouse Schwann cells that senesce after 3-4 passages, these cells are immortalized and fail to arrest at high density (FIG. 7 C, D). However, they retain expression of the Schwann cell marker, S100. Control nf2$^{flox2/flox2}$ Schwann cells transduced with GFP-expressing adenovirus do not undergo these changes (data not shown). In summary, these functional Merlin-null Schwann cells replicate the phenotype of human schwannoma cells and are a novel and valuable tool for the study of NF2 pathogenesis.

11.1 Plate Selection, Cell Density and DMSO Tolerance.

Figure 8:
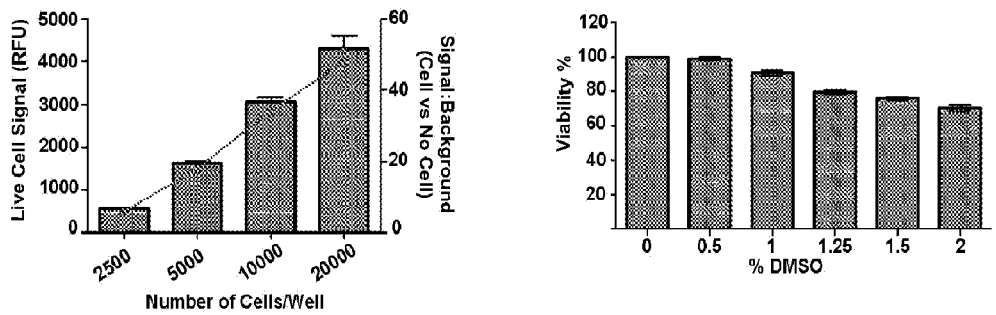
FIG. 8: Optimization of Cell Seeding Density and Evaluation of DMSO Tolerance. A) The effect of cell seeding density on basal cell viability signal of Merlin-null Schwann cells was measured. Cells were plated as described above in 20 ul of DMEM/F12 medium (1:1) with N2 supplements and pen/strep. Fluorescence (405 nmEx/492 nmEm) for live cells, and (485 nmex/535 nmEm) for dead cells was read 30 minutes later. Results of a representative experiment in which cell viability, expressed as RFU (relative fluorescent units), is shown. Signal:background is shown in red. B) Effect of DMSO (0-2.0% v/v) on basal cell viability signal is expressed as percent viability with respect to control (0% DMSO). Ex; excitation, Em; emission.

To ascertain whether this cell line was amenable to a HTS platform, the present inventors tested cell adherence and growth on several types of 384-well plates. Wells were seeded at varying cell densities (2,500-20,000 cells/well) and the ratio of live:dead cells was measured 24 hours later using the MultiTox-Fluor Multiplex Cytotoxicity Assay (Promega). This assay uses fluorescent probes to measure protease activities from live and dying cells. The results indicate that uncoated Corning-Cell Bind plates seeded at 5,000 cells/well is suitable for 24 hour assays. They also carried out a DMSO tolerance test and found a 10% loss of cell viability at 1% DMSO (FIG. 8). Therefore, the DMSO concentration for screening will be maintained at 0.5%.

11.2 Assay Validation.

To evaluate readiness of the MultiTox-Fluor assay, it was tested in a 384-well plate using 5,000 Merlin-null Schwann cells/well treated with increasing concentration of rapamycin, an mTOR inhibitor, in a total volume of 25 µl. The results of the live cell protease (expressed as % of DMSO control) and dead cell protease assay (expressed as relative fluorescence intensity) are shown in FIG. 9A. Viability of cells treated with 50 µM rapamycin was 20+/−1.4% of the DMSO control. Statistical analysis of a control 384-well plate in which only the positive and negative controls were run is shown in FIG. 9B. The Z', calculated using the standard formula, was equal to 0.61 with a signal window of 17[28].

11.3 Pilot Screen of LOPAC in a 384-Well Format.

Figure 9:
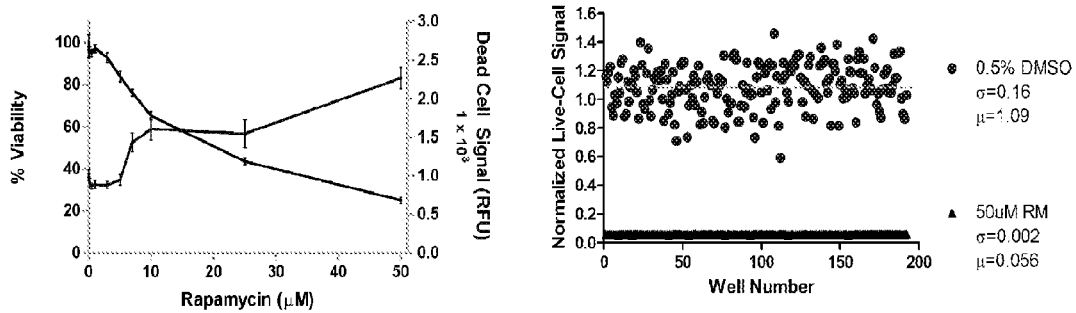
FIG. 9: Demonstration of MultiTox-Fluor Assay Readiness Using Rapamycin and Merlin-Null Schwann Cells in a 384-well Plate. Merlin-null Schwann cells were seeded at 5,000 cells/well in an uncoated Corning Cell-Bind 384-well plate. A) Result of a rapamycin dose response study conducted with the MultiTox-Fluor assay is shown. B) Cell viability in the presence of 0.5% DMSO or 0.5% DMSO plus 50 µM rapamycin (RM) added 4 hours after plating was measured 24 hours later as described in the FIG. 9 legend.

A pilot screen of Sigma's LOPAC was conducted to test the reliability of our system. The 1280 compounds were tested at 10 µM in 0.5% DMSO in single wells. They were added 4 hours after cell plating and the MultiTox-Fluor assay was run 24 hours later. The positive control included cells treated with 50 µM rapamycin in 0.5% DMSO and the negative control included cells treated with 0.5% DMSO. The signals for live and dead protease activities were collected sequentially. The statistics for 4 plates are shown in Table 1 and demonstrate consistency between plates and a Z'=~0.8 for the live cell assay but <0.5 for the dead cell assay. The screen yielded 40 hits using a cut-off value equal to 80% of the live:dead signal of the rapamycin positive control which was equivalent to 50% of live cell signal (FIG. 9). The hits represent a spectrum of compounds that fall into 5 basic categories; 1) inhibitors of signaling kinases, 2) cell-cycle inhibitors, 3) pro-apoptotic agents, 4) receptor inhibitors and 5) modulators of cell metabolism.

TABLE 1

| Merlin-Null SC Live Cell Assay Performance | | | | |
|---|---|---|---|---|
| LOPAC Plate ID | Z' | S/B | Signal Window | Hit Rate |
| PN-019824 | 0.833 | 12.1 | 15.9 | 12 |
| PN-019824 | 0.877 | 12.8 | 23.6 | 12 |
| PN-019824 | 0.796 | 12.5 | 13.4 | 13 |
| PN-019824 | 0.834 | 13.5 | 18.3 | 35 |
| Screen Total | 0.835 | 12.7 | 17.8 | 4.6% |

11.4 Compound Confirmation and Demonstration of Cell Line Reliability.

To demonstrate the reliability of the Merlin-null Schwann cells through various passages and independent derivations, the present inventors measured the effect of AKG2, a compound identified in the LOPAC screen, on viability of Merlin-null Schwann cells at passage 12 and 18 of one derivation and passage 14 of another derivation using CellTiter-Fluor, the Live Cell Protease Assay of the MutliTox-Fluor assay used above. The results demonstrate that a similar loss of viability was obtained with two lines at passage 8-16. Moreover, the percent viability was equivalent that observed for AGK2 in the LOPAC screen which was conducted with L1P23 Merlin-null Schwann cells.

Figure 10:
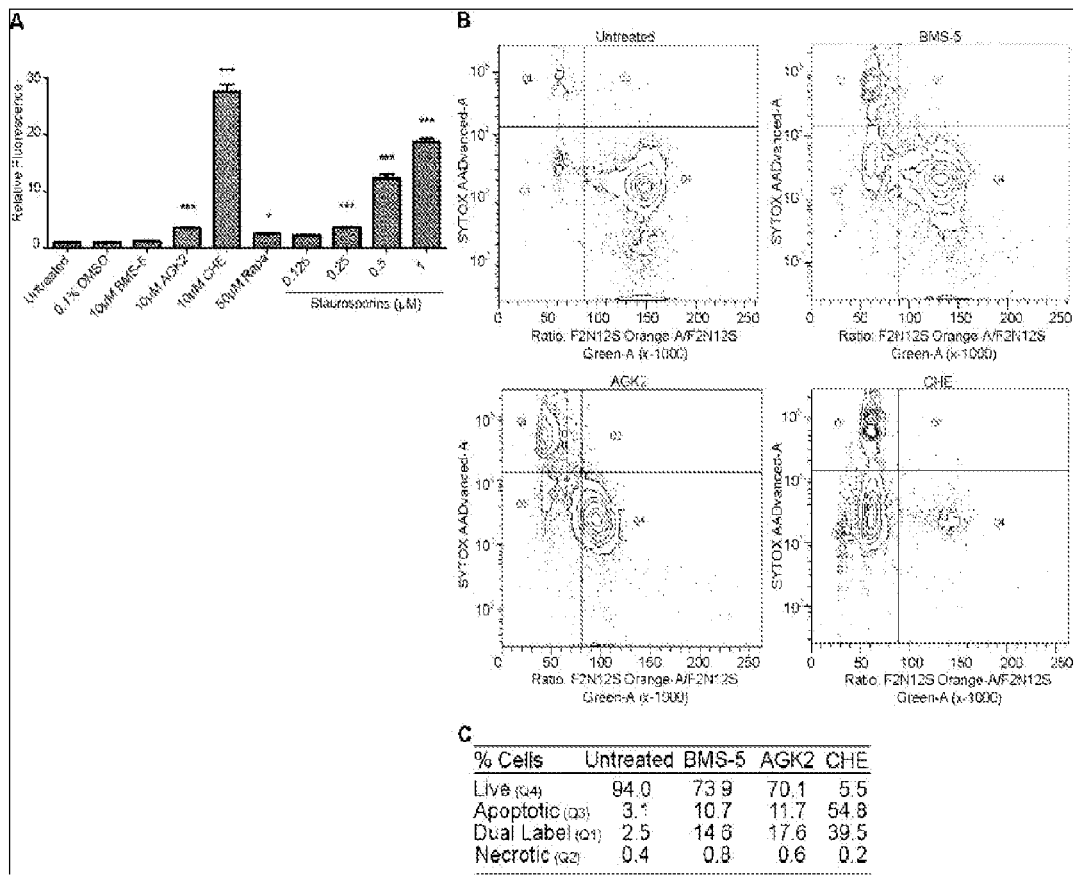
FIGS. 10 A-C. Phenotypic Apoptosis Assays. (A). Merlin-null Schwann cells in a 384-well format were incubated with the indicated compounds for 8 hours. Caspase-3/7 activity was measure with Apo-ONE Homogeneous Assay (Promega). n=32 wells. (B). Merlin-null Schwann cells in a 6-well format were treated with compounds (10 uM) for 24 hours. Membrane asymmetry was detected with Violet Ratiometric assay and read on a BD Cantos II flow cytometer. (C). Population distribution for B is shown.

11.5 Hit Confirmation Assays on Advanced Compounds Using Phenotypic and Merlin Pathway Assays In yet another aspect, compounds may be identified which induce programmed cell death or inhibit proliferation of Merlin-null Schwann cells. Merlin-pathway assays may be conducted to identify the subset of compounds that modulate the activity of known merlin pathways. The effector caspase cascade is activated in many extrinsic and intrinsic cell death pathways[29]. The CPCCG has an established HTS assay that measures caspase-3 activity based on the cleavage and enzymatic degradation of a fluorescent substrate containing the amino acid motif DEVD (DEVD-7-amino-4-trifluoromethyl coumarin, DEVD-AFC). Briefly, Merlin-null Schwann cells may be dispensed and test compounds added, and incubated as described for the primary screening assay. The effect of compounds on caspase-3 activity can be measured by first lysing the cells and centrifuging to pellet the debris. Next, 20 µl of 2× reaction buffer may be added, followed by 1 µL, DTT (0.01M final). Finally, 1uL of DEVD-AFC may be added and the plate may be incubated at 37° C. for 1.5 h. Enzyme activity may be measured on an Envision plate reader at Ex400 nm/Em505 nm. The enzyme activity may be calculated from a standard curve generated using recombinant caspase-3 enzyme (R&D System, Inc.) and expressed as fold-increase in activity. As a follow-up assay, a flow-cytometer based assay may be conducted that measures lipid asymmetry of the plasma membrane, a consequence of most programmed cell death pathways[29]. This assay will confirm the positive results of the Caspase-3 assay, but importantly will identify compounds that trigger caspase-3 independent apoptosis, as well as those that trigger necrosis of Merlin-null Schwann cells. The Violet Ratiometric Membrane Asymmetry Probe/Dead Cell Apoptosis assay (Life Sciences) uses a novel violet dye, 4'-N,N-diethylamino-6-(N,N,N-dodecyl-methylamino-sulfopropyl)-methyl-3-hydroxyflavone (F2N12S). Transfer of phosphatidylserine and phosphatidylethanolamine from the inner to the outer leaflet of the plasma membrane changes the membrane potential that is detected by F2N12S. The dye undergoes an excited-state intramolecular proton transfer (ESIPT) when excited with a 405 laser and emits at both 530 and 585 nm. By calculating the ratio of 585/530 emission, an accurate absolute measure of membrane asymmetry is obtained. Necrotic cells do not exhibit changes in membrane asymmetry and are stained only with SYTOX AADvanced Dead Cell Stain that binds DNA. It is excited at 488 nm and emits at 695 nm. A test was conducted using the Violet Ratiometric Assay and a commercially available caspase-3/7 assay (Apo-ONE Homogeneous Assay, Promega) in a 384-well plate format with Merlin-null Schwann cells (FIG. 10). Three compounds, BMS-5 and AGK2 and cheleryithrine chloride (CHE), an activator of Caspase-3 and protein kinase C identified in the LOPAC screen, were used as a positive control for apoptosis[30,31]. The flow cytometer results demonstrate that CHE induced apoptotic death (Q1+Q3) of 93% of the Merlin-null Schwann cells. Both BMS-5 and AGK2 promoted apoptotic death of a subset (24-30%) of cells during the 24 hour period. In context of the Apo-One assay result, the mechanisms appear to be caspase3/7-independent and possibly secondary to their mechanism of action. Necrotic cells (Q2) were not observed in any condition. Compounds that induce caspase-3/7 activity by 80% of the CHE control in the Apo-ONE or DEVD assay and apoptotic death of over 50% of the cell population in the Violet Ratiometric assay may be considered potential pro-apoptotic "MERLIN" pathway compounds.

11.6 Identification of Anti-Proliferative Compounds

In yet another aspect, identification of compounds that affect proliferation of Merlin-null mouse Schwann cells can be performed by conducting a Click-iT EdU Microplate Assay (Life Technologies) in the 384 well-plate format and then follow-up with BrdU/7AAD and propidium iodide flow cytometer assays. FIG. 11A-D depict results obtained with Merlin-null Schwann cells and BMS-5, AGK2 and CHE. The EdU-Click-iT assay uses a 2-step procedure to identify cells in the S-phase of the cell cycle. EdU (5-ethynyl-2'-deoxyuridine) is a DNA analog that has been modified with an alkyne and is incorporated by cells in S phase. It reacts with Alexa-Fluor-Oregon green azide in the presence of a copper solution to form a covalent bond. Fluorescence emission is measured on a Hybrid HT plate reader (FIG. 11A) as well as on a Trophos Plate RUNNER HD that captures images of the wells (FIG. 11B). This allows confirmatory cell counts to be obtained. Cell cycle profiles were collected using propidium iodide (PI) labeling of log-phase growing Merlin-null Schwann cells (FIG. 11C). The results were confirmed by acquiring the ratio of BrdU-positive to total 7AAD-labelled cells in an independent assay (FIG. 11D). The results show that both BMS-5 and CHE promoted a 40-60% decrease in EdU-labelled cells compared to controls. The PI labeling and BrdU profiles indicate that BMS-5 treated cells accumulate in G2/M and have increased numbers of apoptotic cells and cells with increased DNA content (right side scatter in D). AGK2, with the parameters used (24 hours of drug treatment and S-phase labelling for the final 3 hours), did not reveal clear anti-proliferative effects on the cells. Compounds exhibiting a 50% reduction in EdU and BrdU incorporation compared to controls and statistically significant change in PI profile will be considered potential "MERLIN" pathway compounds.

To further characterize advanced compounds, there are a number of commercially available HTS assays that may be used and measure activity of signaling cascades regulated by merlin. These include: the Rac-Pak-JNK, Ras-ERK, mTOR and the emerging Mst (the eponymous Hippo in *Drosophila*)-YAP pathway that signals cell density changes. To date, there are standardized assays available for all but the Mst-Yap cascade. For example, validated HTS assays are available for: MTOR assay (DiscoverX), RAC (Cytoskeleton, Inc), RAS[32], Erk (CisBio Bioassays), JNK (Perkin Elmer).

REFERENCES

All references set forth herein in this document are incorporated by reference herein to the extent that the subject matter therein does not conflict with the existing disclosure.
1. Manetti, Fabrizio, LIMK Kinases Are Attractive Targets with Many Macromolecular Partners and Only a Few Small Molecule. Published online in Wiley Online Library (wileyonlinelibrary.com) DOI 10.1002/med.20230.
2. Ross-McDonald, P., de Silva, H., Guo, Q., Xiao, H., Hung, C., Penhallow, B., Markwalder, J., He, L., Attar, R., Lin, T., Seitz, S. Tifford, C., Wardwell-Swanson, J., Jackson, D., Identification of a nonkinase target mediating cytotoxicity of novel kinase inhibitors, Mol Cancer Ther 2008:7(11). Nov. 2008.
3. Scott, R., Hooper, S., Crighton, D., Li, A., Konig, I, Munro, J., Trivier, E., Wickman, G., Morin, P., Croft, D., Dawson, J., Machesky, L., Anderson, K, Sahai, E., Olson, M., LIM kinases are required for invasive path generation by tumor and tumor-associated stromal cells.
4. Ozawa, T., Araki N., Yunoue S., Tokuo F L, Feng L., Patrakitkomjorn S., Hara T., Ichikawa Y., Matsumoto K., Fujii K., and Saya H., The Neurofibromatosis Type 1 gene product neurofibromin enhances cell motility by regulating actin filament dynamics via the Rho-ROCK-LIMK2-cofilin pathway. 2005 J. Biol Chem Vol. 280:39524-39533.

It should be borne in mind that all patents, patent applications, patent publications, technical publications, scientific publications, and other references referenced herein and in the accompanying appendices are hereby incorporated by reference in this application to the extent not inconsistent with the teachings herein.

It is important to an understanding to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments have been shown and described herein in the present context, such embodiments are provided by way of example only, and not of limitation. Numerous variations, changes and substitutions will occur to those of skilled in the art without materially departing from the invention herein. For example, the present invention need not be limited to best mode disclosed herein, since other applications can equally benefit from the teachings. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

What is claimed is:

1. A method for treating a neurofibromatosis in a subject, the method comprising administering to the subject an effective amount of a LIMK modulating agent, wherein the LIMK modulating agent specifically inhibits activity of LIMK-1 (SEQ ID NO. 1), wherein the neurofibromatosis comprises a tumor of Schwann cell origin.

2. The method of claim 1, wherein the neurofibromatosis is type 1 Neurofibromatosis (NF1).

3. The method of claim 1, wherein the neurofibromatosis is type 2 Neurofibromatosis (NF2).

4. The method of claim 1, wherein the neurofibromatosis is Schwannomatosis.

5. The method of claim 1, wherein the neurofibromatosis includes sporadic Schwannoma.

6. The method of claim 1, wherein the LIMK modulating agent is selected from the group consisting of a ribozyme, an interfering molecule, a peptide, a small molecule, an antibody targeted to LIMK, and combinations thereof.

7. The method of claim 6, wherein the LIMK modulating agent comprises BMS-5 or prodrug, analog, derivative, metabolite, and/or pharmaceutically acceptable salt thereof.

8. The method of claim 1, wherein the LIMK modulating agent comprises an interfering molecule, and wherein the interfering molecule comprises a member selected from the group consisting of a phosphothioate morpholino oligomer (PMO), miRNA, sRNA, methylated sRNA, treated siRNAs, shRNA, antisense RNA, a dicer-substrate 27-mer duplex, and combinations thereof.

9. The method of claim 1, wherein the subject exhibits a symptom of a neurofibromatosis.

10. The method of claim 9, wherein the symptom comprises a presence of multiple coffee-colored patches on a skin of the subject, hearing loss or disequilibrium, or a combination thereof.

11. The method of claim 1, wherein the LIMK modulating agent comprises BMS-5, or prodrug, analog, derivative, metabolite, and/or pharmaceutically acceptable salt thereof.

12. A method of inhibiting Schwann cell proliferation in a subject comprising administering an effective amount of an LIMK modulating agent, or prodrug, analog, derivative, metabolite, and/or pharmaceutically acceptable salt thereof, to the subject to inhibit the expression or action of LIMK (SEQ ID NO. 1).

13. The method of claim 12, wherein the LIMK modulating agent is selected from the group consisting of a ribozyme, an interfering molecule, a peptide, a small molecule, or an antibody targeted to LIMK.

14. The method of claim 12, wherein the LIMK modulating agent comprises BMS-5, or prodrug, analog, derivative, metabolite, and/or pharmaceutically acceptable salt thereof.

15. The method of claim 12, wherein the LIMK modulating agent comprises an interfering molecule.

16. The method of claim 15, wherein the interfering molecule comprises a member selected from the group consisting of a phosphothioate morpholino oligomer (PMO), miRNA, sRNA, methylated sRNA, treated siRNAs, shRNA, antisense RNA, a dicer-substrate 27-mer duplex, and any combination thereof.

* * * * *

SEQUENCE LISTING

```
<160> NUMBER OF SEQ ID NOS: 2

<210> SEQ ID NO 1
<211> LENGTH: 613
<212> TYPE: PRT
<213> ORGANISM: homo sapiens

<400> SEQUENCE: 1

Met Leu Leu Ala Ser Ala Pro Arg Arg Arg Phe Leu Gln Arg Ala
1               5                   10                  15

Lys Cys Cys Asp Cys Ser Ala Ser Leu Ser His Gln Tyr Tyr Glu Lys
                20                  25                  30

Asp Gly Gln Leu Phe Cys Lys Lys Asp Tyr Trp Ala Arg Tyr Gly Glu
                35                  40                  45

Ser Cys His Gly Cys Ser Glu Gln Ile Thr Lys Gly Leu Val Met Val
50                      55                      60

Ala Gly Glu Leu Lys Tyr His Pro Glu Cys Phe Ile Cys Leu Thr Cys
65                      70                      75                  80

Gly Thr Phe Ile Gly Asp Gly Asp Thr Tyr Thr Leu Val Glu His Ser
                85                      90                      95

Lys Leu Tyr Cys Gly His Cys Tyr Tyr Gln Thr Val Val Thr Pro Val
                100                 105                 110

Ile Glu Gln Ile Leu Pro Asp Ser Pro Gly Ser His Leu Pro His Thr
                115                 120                 125

Val Thr Leu Val Ser Ile Pro Ala Ser Ser His Gly Lys Arg Gly Leu
130                 135                     140

Ser Val Ser Ile Asp Pro Pro His Gly Pro Pro Gly Cys Gly Thr Glu
145                 150                     155                 160

His Ser His Thr Val Arg Val Gln Gly Val Asp Pro Gly Cys Met Ser
                165                     170                 175

Pro Asp Val Lys Asn Ser Ile His Val Gly Asp Arg Ile Leu Glu Ile
                180                     185                 190

Asn Gly Thr Pro Ile Arg Asn Val Pro Leu Asp Glu Ile Asp Leu Leu
                195                 200                     205

Ile Gln Glu Thr Ser Arg Leu Leu Gln Leu Thr Leu Glu His Asp Pro
210                 215                     220

His Asp Thr Leu Gly His Gly Leu Gly Pro Glu Thr Ser Pro Leu Ser
225                     230                     235                 240

Ser Pro Ala Tyr Thr Pro Ser Gly Glu Ala Gly Ser Ser Ala Arg Gln
                245                     250                     255

Lys Pro Val Leu Arg Ser Cys Ser Ile Asp Arg Ser Pro Gly Ala Gly
                260                     265                 270

Ser Leu Gly Ser Pro Ala Ser Gln Arg Lys Asp Leu Gly Arg Ser Glu
                275                     280                 285

Ser Leu Arg Val Val Cys Arg Pro His Arg Ile Phe Arg Pro Ser Asp
                290                 295                     300

Leu Ile His Gly Glu Val Leu Gly Lys Gly Cys Phe Gly Gln Ala Ile
305                     310                     315                 320
```

```
Lys Val Thr His Arg Glu Thr Gly Glu Val Met Val Met Lys Glu Leu
                325                 330                 335

Ile Arg Phe Asp Glu Glu Thr Gln Arg Thr Phe Leu Lys Glu Val Lys
            340                 345                 350

Val Met Arg Cys Leu Glu His Pro Asn Val Leu Lys Phe Ile Gly Val
                355                 360                 365

Leu Tyr Lys Asp Lys Arg Leu Asn Phe Ile Thr Glu Tyr Ile Lys Gly
            370                 375                 380

Gly Thr Leu Arg Gly Ile Ile Lys Ser Met Asp Ser Gln Tyr Pro Trp
385                 390                 395                 400

Ser Gln Arg Val Ser Phe Ala Lys Asp Ile Ala Ser Gly Met Ala Tyr
                405                 410                 415

Leu His Ser Met Asn Ile Ile His Arg Asp Leu Asn Ser His Asn Cys
            420                 425                 430

Leu Val Arg Glu Asn Lys Asn Val Val Ala Asp Phe Gly Leu Ala
            435                 440                 445

Arg Leu Met Val Asp Glu Lys Thr Gln Pro Glu Gly Leu Arg Ser Leu
    450                 455                 460

Lys Lys Pro Asp Arg Lys Lys Arg Tyr Thr Val Val Gly Asn Pro Tyr
465                 470                 475                 480

Trp Met Ala Pro Glu Met Ile Asn Gly Arg Ser Tyr Asp Glu Lys Val
                485                 490                 495

Asp Val Phe Ser Phe Gly Ile Val Leu Cys Glu Ile Ile Gly Arg Val
            500                 505                 510

Asn Ala Asp Pro Asp Tyr Leu Pro Arg Thr Met Asp Phe Gly Leu Asn
            515                 520                 525

Val Arg Gly Phe Leu Asp Arg Tyr Cys Pro Pro Asn Cys Pro Pro Ser
    530                 535                 540

Phe Phe Pro Ile Thr Val Arg Cys Cys Asp Leu Asp Pro Glu Lys Arg
545                 550                 555                 560

Pro Ser Phe Val Lys Leu Glu His Trp Leu Glu Thr Leu Arg Met His
                565                 570                 575

Leu Ala Gly His Leu Pro Leu Gly Pro Gln Leu Glu Gln Leu Asp Arg
            580                 585                 590

Gly Phe Trp Glu Thr Tyr Arg Arg Gly Glu Ser Gly Leu Pro Ala His
            595                 600                 605

Pro Glu Val Pro Asp
    610

<210> SEQ ID NO 2
<211> LENGTH: 638
<212> TYPE: PRT
<213> ORGANISM: homo sapiens

<400> SEQUENCE: 2

Met Ser Ala Leu Ala Gly Glu Asp Val Trp Arg Cys Pro Gly Cys Gly
1               5                   10                  15

Asp His Ile Ala Pro Ser Gln Ile Trp Tyr Arg Thr Val Asn Glu Thr
            20                  25                  30

Trp His Gly Ser Cys Phe Arg Cys Ser Glu Cys Gln Asp Ser Leu Thr
            35                  40                  45

Asn Trp Tyr Tyr Glu Lys Asp Gly Lys Leu Tyr Cys Pro Lys Asp Tyr
    50                  55                  60

Trp Gly Lys Phe Gly Glu Phe Cys His Gly Cys Ser Leu Leu Met Thr
65                  70                  75                  80
```

```
Gly Pro Phe Met Val Ala Gly Glu Phe Lys Tyr His Pro Glu Cys Phe
             85                  90                  95

Ala Cys Met Ser Cys Lys Val Ile Ile Glu Asp Gly Asp Ala Tyr Ala
            100                 105                 110

Leu Val Gln His Ala Thr Leu Tyr Cys Gly Lys Cys His Asn Glu Val
            115                 120                 125

Val Leu Ala Pro Met Phe Glu Arg Leu Ser Thr Glu Ser Val Gln Glu
        130                 135                 140

Gln Leu Pro Tyr Ser Val Thr Leu Ile Ser Met Pro Ala Thr Thr Glu
145                 150                 155                 160

Gly Arg Arg Gly Phe Ser Val Ser Val Glu Ser Ala Cys Ser Asn Tyr
                165                 170                 175

Ala Thr Thr Val Gln Val Lys Glu Val Asn Arg Met His Ile Ser Pro
            180                 185                 190

Asn Asn Arg Asn Ala Ile His Pro Gly Asp Arg Ile Leu Glu Ile Asn
        195                 200                 205

Gly Thr Pro Val Arg Thr Leu Arg Val Glu Glu Val Glu Asp Ala Ile
    210                 215                 220

Ser Gln Thr Ser Gln Thr Leu Gln Leu Leu Ile Glu His Asp Pro Val
225                 230                 235                 240

Ser Gln Arg Leu Asp Gln Leu Arg Leu Glu Ala Arg Leu Ala Pro His
                245                 250                 255

Met Gln Asn Ala Gly His Pro His Ala Leu Ser Thr Leu Asp Thr Lys
            260                 265                 270

Glu Asn Leu Glu Gly Thr Leu Arg Arg Arg Ser Leu Arg Arg Ser Asn
        275                 280                 285

Ser Ile Ser Lys Ser Pro Gly Pro Ser Ser Pro Lys Glu Pro Leu Leu
    290                 295                 300

Phe Ser Arg Asp Ile Ser Arg Ser Glu Ser Leu Arg Cys Ser Ser Ser
305                 310                 315                 320

Tyr Ser Gln Gln Ile Phe Arg Pro Cys Asp Leu Ile His Gly Glu Val
                325                 330                 335

Leu Gly Lys Gly Phe Phe Gly Gln Ala Ile Lys Val Thr His Lys Ala
            340                 345                 350

Thr Gly Lys Val Met Val Met Lys Glu Leu Ile Arg Cys Asp Glu Glu
        355                 360                 365

Thr Gln Lys Thr Phe Leu Thr Glu Val Lys Val Met Arg Ser Leu Asp
    370                 375                 380

His Pro Asn Val Leu Lys Phe Ile Gly Val Leu Tyr Lys Asp Lys Lys
385                 390                 395                 400

Leu Asn Leu Leu Thr Glu Tyr Ile Glu Gly Thr Leu Lys Asp Phe
                405                 410                 415

Leu Arg Ser Met Asp Pro Phe Pro Trp Gln Gln Lys Val Arg Phe Ala
            420                 425                 430

Lys Gly Ile Ala Ser Gly Met Ala Tyr Leu His Ser Met Cys Ile Ile
        435                 440                 445

His Arg Asp Leu Asn Ser His Asn Cys Leu Ile Lys Leu Asp Lys Thr
    450                 455                 460

Val Val Val Ala Asp Phe Gly Leu Ser Arg Leu Ile Val Glu Glu Arg
465                 470                 475                 480

Lys Arg Ala Pro Met Glu Lys Ala Thr Thr Lys Lys Arg Thr Leu Arg
                485                 490                 495
```

```
Lys Asn Asp Arg Lys Lys Arg Tyr Thr Val Val Gly Asn Pro Tyr Trp
            500             505             510
Met Ala Pro Glu Met Leu Asn Gly Lys Ser Tyr Asp Glu Thr Val Asp
        515             520             525
Ile Phe Ser Phe Gly Ile Val Leu Cys Glu Ile Ile Gly Gln Val Tyr
        530             535             540
Ala Asp Pro Asp Cys Leu Pro Arg Thr Leu Asp Phe Gly Leu Asn Val
545             550             555             560
Lys Leu Phe Trp Glu Lys Phe Val Pro Thr Asp Cys Pro Pro Ala Phe
            565             570             575
Phe Pro Leu Ala Ala Ile Cys Cys Arg Leu Glu Pro Glu Ser Arg Pro
        580             585             590
Ala Phe Ser Lys Leu Glu Asp Ser Phe Glu Ala Leu Ser Leu Tyr Leu
        595             600             605
Gly Glu Leu Gly Ile Pro Leu Pro Ala Glu Leu Glu Glu Leu Asp His
        610             615             620
Thr Val Ser Met Gln Tyr Gly Leu Thr Arg Asp Ser Pro Pro
625             630             635
```